(12) United States Patent
Blank et al.

(10) Patent No.: US 7,053,178 B2
(45) Date of Patent: May 30, 2006

(54) SYNTHETIC PEPTIDES AND KITS FOR DIAGNOSIS OF ANTI-PHOSPHOLIPID SYNDROME

(75) Inventors: Miri Blank, Tel-Aviv (IL); Shmuel Cabilly, Gedera (IL); Yehuda Shoenfeld, Ramat Gan (IL); Ephraim Katchalski-Katzir, Rehovot (IL)

(73) Assignee: Yeda Research Development Co., LTD, Rehovot (IL)

( * ) Notice: Subject to any disclaimer, the term of this patent is extended or adjusted under 35 U.S.C. 154(b) by 0 days.

(21) Appl. No.: 10/997,989

(22) Filed: Nov. 29, 2004

(65) Prior Publication Data

US 2005/0107584 A1    May 19, 2005

Related U.S. Application Data

(62) Division of application No. 09/743,225, filed as application No. PCT/IL99/00366 on Jul. 6, 1999, now Pat. No. 6,825,319.

(30) Foreign Application Priority Data

Jul. 7, 1998    (IL) ..................................... 125262

(51) Int. Cl.
   *C07K 7/00*    (2006.01)
(52) U.S. Cl. ...................... 530/328; 530/329; 530/345; 514/15; 514/16; 514/17
(58) Field of Classification Search ............... 530/328, 530/329, 345; 514/15, 16, 17
See application file for complete search history.

(56) References Cited

U.S. PATENT DOCUMENTS

| 4,141,880 A | 2/1979 | Nametz et al. |
| 6,414,112 B1 | 7/2002 | Buchardt et al. |

FOREIGN PATENT DOCUMENTS

| EP | 0 821 003 A1 | 1/1998 |
| WO | WO 98/21233 | 5/1998 |

OTHER PUBLICATIONS

Wang M X et al: "Epitope specificity of monoclonal anti-beta 2-glycoprotein 1 antibodies derived from patients wiht the antiphospholipid syndrome.", Journal of Immkunology, (Aug. 1, 1995) 155 (3) 1629-36., XP002125557.

George E.A.: "Differential effects of anti-beta-2-glycoprotein 1 antibodies on endothelial cells and on the manifestations of experimental antiphospholipid syndrome", Circulation vol. 97, No. 9, Mar. 10, 1998, p. 900-906.

Blank E.A.: "Prevention of experimental antiphospholipid syndrome and endothelial cell activation by synthetic peptides", Proceedings of the National Academy of Sciences Of USA, vol. 96, Apr. 1999, pp. 5164-5168, XP00212556.

*Primary Examiner*—David Lukton
(74) *Attorney, Agent, or Firm*—Browdy and Neimark PLLC

(57) ABSTRACT

Synthetic peptides and derivatives thereof capable of inhibiting the biological activity of anti-beta-2-glycoprotein 1 (β2GPI) monoclonal antibodies (mAbs) in vitro, and of inhibiting induction of experimental anti-phospholipid syndrome (APS) in mice by anti-β2GPI mAbs, are provided for the diagnosis and treatment of anti-phospholipid syndrome in humans.

8 Claims, 16 Drawing Sheets

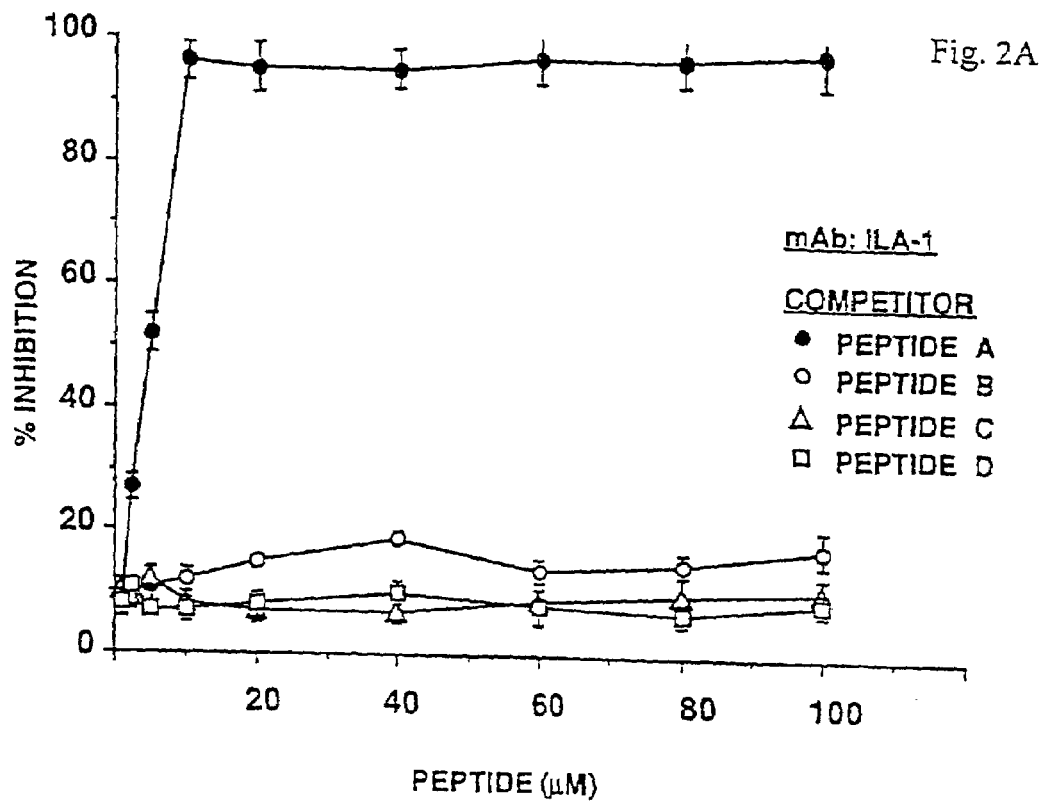
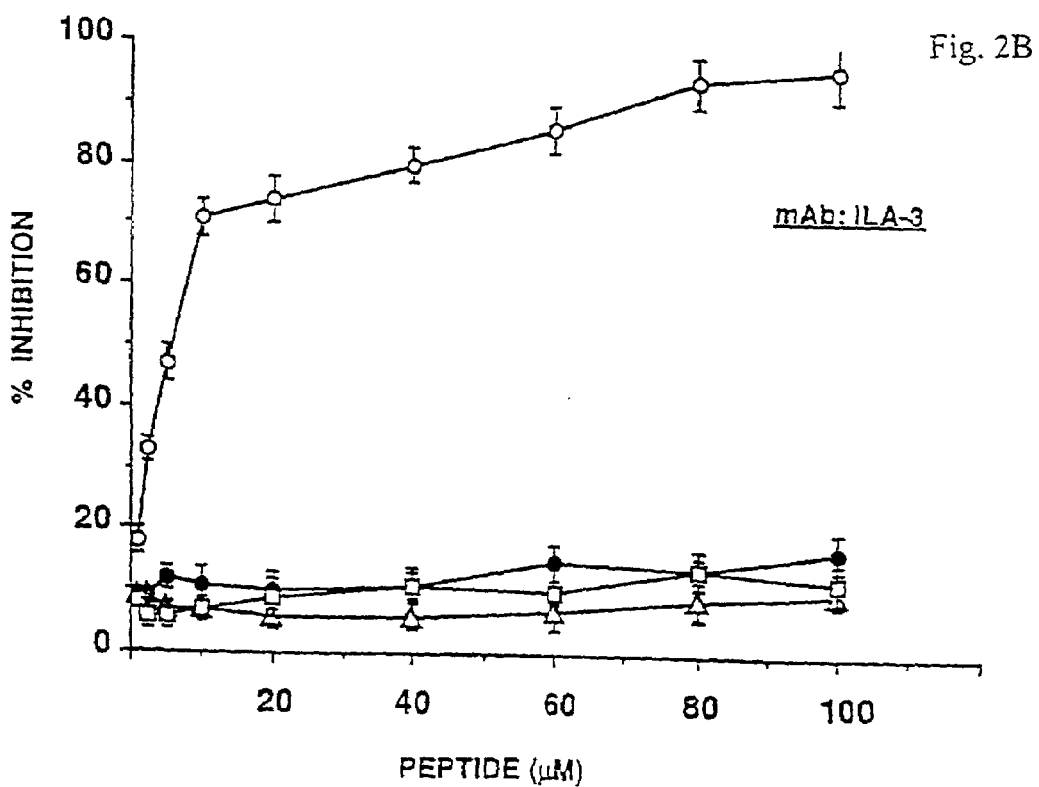

SEQUENCE LISTING

```
<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: synthetic

<400> SEQUENCE: 1

Leu Lys Thr Pro Arg Val
1               5

<210> SEQ ID NO 2
```

```
<211> LENGTH: 6
<212> TYPE: PRT
<213> ORGANISM: Artificial Sequence
<220> FEATURE:
<223> OTHER INFORMATION: synthetic

<400> SEQUENCE: 2

Lys Thr Pro Arg Val Thr
1               5

<210> SEQ ID NO 3
<211> LENGTH: 10
<212> TYPE: PRT
<213> ORGANISM: Artificial Sequence
<220> FEATURE:
<223> OTHER INFORMATION: synthetic

<400> SEQUENCE: 3

Asn Thr Leu Lys Thr Pro Arg Val Gly Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic

<400> SEQUENCE: 4

Lys Asp Lys Ala Thr Phe Gly Thr His Asp Gly
1               5                   10

<210> SEQ ID NO 5
<211> LENGTH: 6
<212> TYPE: PRT
<213> ORGANISM: Artificial Sequence
<220> FEATURE:
<223> OTHER INFORMATION: synthetic

<400> SEQUENCE: 5

Thr Lys Leu Arg Val Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic

<400> SEQUENCE: 6

Thr Leu Leu Arg Val Tyr
1               5

<210> SEQ ID NO 7
<211> LENGTH: 10
<212> TYPE: PRT
<213> ORGANISM: Artificial Sequence
<220> FEATURE:
<223> OTHER INFORMATION: synthetic

<400> SEQUENCE: 7

Cys Ala Thr Leu Arg Val Tyr Lys Gly Gly
1               5                   10

<210> SEQ ID NO 8
<211> LENGTH: 12
```

```
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa is FmocLys(Fmoc)-OH

<400> SEQUENCE: 8

Asn Thr Leu Lys Thr Pro Arg Val Gly Gly Xaa Ala
1               5                   10

<210> SEQ ID NO 9
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa is FmocLys(Fmoc)-OH

<400> SEQUENCE: 9

Lys Asp Lys Ala Thr Phe Gly Thr His Asp Gly Gly Xaa Ala
1               5                   10

<210> SEQ ID NO 10
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa is FmocLys(Fmoc)-OH

<400> SEQUENCE: 10

Cys Ala Thr Leu Arg Val Tyr Lys Gly Gly Gly Xaa Ala
1               5                   10

<210> SEQ ID NO 11
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: Xaa is FmocLys(Fmoc)-OH

<400> SEQUENCE: 11

Pro Val Arg Ser Pro His Gln Ser Tyr Pro Gly Gly Gly Xaa Ala
1               5                   10                  15

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Lys Thr Pro Arg Val Thr
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: synthetic

<400> SEQUENCE: 13

Lys Asp Lys Ala Thr Phe
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic

<400> SEQUENCE: 14

Thr Leu Arg Val Tyr Lys
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic

<400> SEQUENCE: 15

Thr Lys Leu Arg Val Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: synthetic

<400> SEQUENCE: 16

Thr Leu Leu Arg Val Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic

<400> SEQUENCE: 17

Leu Lys Cys Thr Pro Arg Val
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic

<400> SEQUENCE: 18

Lys Cys Thr Pro Arg Val Cys Cys Thr
1               5

<210> SEQ ID NO 19
```

```
<211> LENGTH: 6
<212> TYPE: PRT
<213> ORGANISM: Artificial Sequence
<220> FEATURE:
<223> OTHER INFORMATION: synthetic

<400> SEQUENCE: 19

Leu Val Glu Pro Trp Arg
1               5
```

SYNTHETIC PEPTIDES AND KITS FOR DIAGNOSIS OF ANTI-PHOSPHOLIPID SYNDROME

CROSS-REFERENCE TO RELATED APPLICATIONS

The present application is a divisional of application Ser. No. 09/743,225, filed Jan. 8, 2001 now U.S. Pat. No. 6,825,319, which is a 371 national stage application of PCT/IL99/00366, filed Jul. 6, 1999, the entire contents of which are hereby incoporated by reference. Application PCT/IL99/00366 claims priority to Israeli application 125262, filed Jul. 7, 1998.

FIELD OF THE INVENTION

The present invention relates to synthetic peptides and to pharmaceutical compositions comprising them for the diagnosis and treatment of anti-phospholipid syndrome.

ABBREVIATIONS: AFC: antibody-forming cells; APS: anti-phospholipid syndrome; HUVEC: human umbilical vein endothelial cells; mAb: monoclonal antibody; MAP: multiple antigenic peptide; PBL: peripheral blood lymphocytes; SLE: systemic lupus erythematosus; St: streptavidin; β2GPI: beta-2-glycoprotein 1.

BACKGROUND OF THE INVENTION

Autoimmune diseases are disorders in which the immune system produces autoantibodies directed against an endogenous antigen, with consequent injury to tissues. These self antigens, called also autoantigens, despite being normal tissue constituents, are the target of a humoral or cell-mediated immune response that characterizes the autoimmune disease.

Several connective tissue disorders including vascular diseases, such as vasculitis, systemic lupus erythematosus (SLE), and polymyositis, neurologic diseases such as multiple sclerosis and myasthenia gravis, and hematologic diseases such as idiopathic thrombocytopenia purpura (ITP) and anti-phospholipid syndrome (APS) seem to be caused by an autoimmune reaction. For some of these disorders, the self antigen has been identified and/or pathogenic autoantibodies have been identified and isolated.

No specific drugs exist nowadays for the treatment of autoimmune diseases and patients are treated with anti-inflammatory drugs such as corticosteroids and/or immunosuppressive drugs. All research being carried out in this field is directed to the development of drugs specific for each disease.

Anti-phospholipid antibodies have been associated with a variety of clinical phenomena, including arterial and venous thrombosis, thrombocytopenia, and obstetric complications. The term "anti-phospholipid syndrome" is used to link a variety of thrombotic events to antibodies against specific proteins involved in blood coagulation. Thrombotic events are reported in approximately 30% of patients with anti-phospholipid antibodies, with an overall incidence of 2.5% patients/year. Deep vein thrombosis of the legs and/or thrombotic events, and cerebral arterial thrombosis are the most common arterial complications. Obstetric complications include recurrent spontaneous miscarriages, fetal deaths, or fetal growth retardations. Women with anti-phospholipid antibodies are particularly prone to second or third trimester fetal death.

The anti-phospholipid syndrome (APS) is characterized by the presence of high titers of anti-cardiolipin and/or anti-β2GPI (beta-2-glycoprotein 1) antibodies which might have lupus anti-coagulant activity leading to thromboembolic phenomena, thrombocytopenia, recurrent fetal loss, as well as other multisystemic involvements. APS can emerge as a primary syndrome or as secondary syndrome to SLE (Hughes et al., 1986; McNeil et al., 1991).

Anti-β2GPI antibodies bind anionic phospholipids through the β2GPI molecule (McNeil et al., 1990; Igarashi et al., 1996). β2GPI is the target antigen for the autoimmune anti-β2GPI antibodies previously entitled 'anti-cardiolipin/anti-phospholipid β2GPI dependent antibodies'. β2GPI (50 KD), initially described by Schultze et al. (1961), is composed of five respective consensus ('sushi' like) repeats (Kandiah and Krilis, 1994). β2GPI binds negatively charged phospholipids through a lysine-rich locus (Cys281–Cys288) located in the fifth domain (Hunt and Krilis, 1994) and possesses several in vitro properties which define it as an anticoagulant, i.e., it causes inhibition of prothrombinase activity, ADP-induced platelet aggregation, platelet factor IX production (Sheng et al., 1996). Employing site-directed mutagenesis of recombinant human β2GPI, a cluster of lysine residues that are critical for phospholipid binding and anti-cardiolipin antibody activity was identified (Sheng et al., 1996).

The anti-β2GPI antibodies have been considered to exert a direct pathogenic effect by interfering with hemostatic reactions occurring on the surface of platelets or vascular endothelial cells (Shi et al, 1993; Simantov et al., 1995). Passive transfer of these antibodies into naive mice or mice prone to develop APS, resulted in induction of experimental APS in mice (Blank et al., 1991). It has been shown recently (Del Papa et al., 1997; George et al., 1998) that human polyclonal and monoclonal anti-β2GPI antibodies react in vitro with endothelial cells through adherent β2GPI and induce differential endothelial cell activation. It is not clear to which epitopes on the β2GPI molecule these anti-β2GPI antibodies are directed, and the correlation to their biological activity.

Attempts have been made to find peptides that could mimic the self antigen-epitope and would inhibit the autoantibody/self antigen binding and consequent injury to the tissue. Thus, recently, peptides selected from phage-epitope libraries through binding to pathogenic monoclonal autoantibodies were shown to provide a surrogate antigen or mimotope that inhibits binding to the original antigen. Such peptides reflect the sequence or conformation of the antigen-binding site, and the fine specificity of the autoantibodies to the protein and non-protein, e.g. polysaccharides or dsDNA, antigens (Scott and Smith, 1990; Scott et al., 1992; Yayon et al., 1993).

SUMMARY OF THE INVENTION

It is an object of the present invention to provide means for diagnosis and specific treatment of the autoimmune disorder anti-phospholipid syndrome (APS).

A further object of the invention is to provide means for inactivating B-cells responsible for the production of autoantibodies appearing in APS patients.

The present invention relates to synthetic peptides suitable for the diagnosis and treatment of APS, more particularly to synthetic peptides and derivatives thereof capable of inhibiting the biological activity of anti-β2GPI mAbs in vitro, and of inhibiting induction of experimental APS in mice by anti-β2GPI mAbs.

In a preferred embodiment, the peptides of the invention and their derivatives are selected from the group consisting of:
  (i) a peptide of at least 4 amino acid residues comprising a sequence selected from:
    (a) Thr-Pro-Arg-Val (residues 1–4 of SEQ ID NO:1)
    (b) Lys-Ala-Thr-Phe (residues 3–6 of SEQ ID NO:4)
    (c) Leu-Arg-Val-Tyr (residues 4–7 of SEQ ID NO:7)
  (ii) a cyclic derivative of a peptide of (i);
  (iii) a peptide according to (i) or (ii) in which one or more amino acid residues have been replaced by the corresponding D-isomer or by a non-natural amino acid residue;
  (iv) a chemical derivative of a peptide according to (i)–(iii);
  (v) a multichain peptide-oligomer/polymer conjugate comprising two or more of the same or different peptides or peptide derivatives (i) to (iv) attached to a native or synthetic multifunctional oligomeric or macromolecular backbone; and
  (vi) a multiple antigen peptide (MAP) in which two to eight same or different peptides or peptide derivatives (i) to (iv) are attached to a diaminoalkanoic acid core.

In one embodiment, a peptide according to (i)(a) above has a sequence selected from:
  (a1) Leu Lys Thr Pro Arg Val (SEQ ID NO:1)
  (a2) Lys Thr Pro Arg Val Thr (SEQ ID NO:2)
  (A) Asn Thr Leu Lys Thr Pro Arg Val Gly Gly (SEQ ID NO:3)

In another embodiment, a peptide according to (i)(b) above has a sequence selected from:
  (b1) Lys Asp Lys Ala Thr Phe (residues 1–6 of SEQ ID NO:4)
  (B) Lys Asp Lys Ala Thr Phe Gly Thr His Asp Gly (SEQ ID NO:4)

In a further embodiment, a peptide according to (i)(c) above has a sequence selected from:
  (c1) Thr Leu Arg Val Tyr Lys (residues 3–8 of SEQ ID NO:7)
  (c2) Thr Lys Leu Arg Val Tyr (SEQ ID NO:5)
  (c3) Thr Leu Leu Arg Val Tyr (SEQ ID NO:6)
  (C) Cys Ala Thr Leu Arg Val Tyr Lys Gly Gly (SEQ ID NO:7)

Peptides (a1), (a2), (b1), (c1), (c2), and (c3) were obtained using a phage display hexapeptide epitope library and, based on their sequences, peptides A, B, and C were synthesized and shown to neutralize the biological activity of the anti-β2GPI antibodies and to elicit antiproliferative B-cell response.

It has further been found according to the present invention that when a number of the same or different peptides or peptide derivatives (i) to (iv) which recognize and bind to autoantibodies secreted by specific B cells in APS are attached to a multifunctional oligomolecular or macromolecular backbone, the resulting molecule according to (v) above (hereinafter designated peptide "dimer", "tetramer", etc.) is capable of inhibiting the production of said autoantibodies by said specific B cells.

The multifunctional oligomolecular or macromolecular backbone may be derived from a native oligomolecular or macromolecular compound such as proteins, oligopeptides, oligosaccharides and oligonucleotides. Suitable proteins are for example albumins, globulins, avidin, and streptavidin.

The multifunctional oligomolecular or macromolecular backbone may also be derived from a non-antigenic synthetic oligomer or polymer such as oligolysine, oligoglutamic acid, linear or branched polylysine, polyglutamic acid or copolymers of those containing optionally further amino acid residues.

In one preferred embodiment, a peptide or peptide derivative of the invention is biotinylated and a multichain peptide-protein conjugate is obtained by linking two or four molecules of the same or different biotinylated peptide to streptavidin or avidin. According to this embodiment, "dimers" and "tetramers" of peptides A, B and C were obtained by attaching 2 or 4 molecules of biotinylated peptides A, B or C, respectively, to one molecule of streptavidin.

The invention further provides multiple antigen peptides (MAPs) according to (vi) above in which two to eight same or different peptides or peptide derivatives (i) to (iv) are anchored onto a small immunogenically inert, two-fold bifurcating diaminoalkanoic acid core. The diaminoalkanoic acid molecule may be ornithine, diaminobutyric acid, homolysine but preferably it is lysine. According to this embodiment, "divalent" and "tetravalent" peptides A, B and C were obtained by attaching 2 or 4 molecules of peptides A, B or C to one or two molecules of FmocLys(Fmoc)-OH via Gly and/or Ala as spacer.

The invention further provides pharmaceutical compositions comprising a peptide or a derivative thereof of the invention and a pharmaceutically acceptable carrier for the treatment of APS, a method for the treatment of APS which comprises administering to a patient in need thereof an effective amount of a peptide or peptide derivative of the invention, and a method for inactivating B cells or killing the specific B cells responsible for the production of autoantibodies appearing in a patient suffering from APS which comprises administering to said patient an effective amount of a multichain peptide or a multiple antigen peptide of the invention.

The invention further provides diagnostic kits comprising one or more peptides or derivatives thereof of the invention, representing target epitopes for the diagnosis of anti-phospholipid antibodies with different pathogenic biofunctions, which may correlate either with pregnancy complications, thrombosis, or coagulation dysregulation. These kits will allow a quicker diagnosis of the presence of specific autoantibodies, and possibility to provide a more specific treatment for patients with anti-phospholipid syndrome.

Definitions

In the description hereinafter the following terminology will be used:

Peptide monomer: a single inhibitory peptide A, B, C or irrelevant peptide D.

Peptide dimer: a conjugate of two molecules of biotinylated peptide monomer A, B, C, or D, with one molecule of streptavidin, herein St-diA, St-diB, St-diC, or St-diD.

Peptide tetramer: a conjugate of four molecules of biotinylated peptide monomer A, B, C, or D, with one molecule of streptavidin, herein St-tetraA, St-tetraB, St-tetraC, or St-tetraD.

Divalent peptide: an MAP obtained by attaching 2 molecules of peptide A, B, C or D to 2 molecules of FmocLys(Fmoc)-OH via Gly and/or Ala as spacer, wherein the protective Fmoc (9-fluorenylmethyloxycarbonyl) group is removed during the process of attaching the desired peptide, thus resulting in divalent peptides represented as Lys(α,ε-diA), Lys(α,ε-diB), Lys(α,ε-diC), or Lys(α,ε-diD), herein "divalent A, B, C or D".

Tetravalent peptide: an MAP obtained by attaching 4 molecules of peptide A, B, C or D to 4 molecules of FmocLys(Fmoc)-OH via Gly and/or Ala as spacer, thus resulting in tetravalent peptides represented as (di-α,ε-Lys)$_2$Lys(tetraA), (di-α,ε-Lys)$_2$Lys(tetraB), (di-α,ε-Lys)$_2$Lys(tetraC), (di-α,ε-Lys)$_2$Lys(tetraD), herein "tetravalent A, B, C or D".

BRIEF DESCRIPTION OF THE DRAWINGS

FIGS. 2A–2C are graphs showing inhibition of the anti-β2GPI ILA-1, ILA-3 and G-3 mAbs binding to human umbilical vein endothelial cells (HUVEC) by competition assays using increasing concentrations of the inhibitory monomer peptides A, B and C, respectively, and of unrelated peptide D as control. The percent of inhibition was calculated as in FIG. 1 above. Each point represents mean±SD of three different experiments.

FIG. 6A: Affinity purified anti-β2GPI IgM and IgG that recognize peptide A were tested for binding to peptide A following preincubation of the purified antibodies with peptide A, cocktail of peptides B+C+D or β2GPI. Each point represents one patient. FIG. 6B: Affinity purified anti-β2GPI IgM and IgG that recognize peptide B were tested for binding to peptide B following preincubation with peptide B, cocktail of peptides A+C+D or β2GPI. Each point represents one patient. FIG. 6C: Affinity purified anti-β2GPI IgM and IgG that recognize peptide C were tested for binding to peptide C following preincubation with peptide C, cocktail of peptides A+B+D or β2GPI. Each point represents one patient.

FIGS. 10 (A–C) show in vitro effect of the inhibitory peptides on human anti-β2GPI AFC activity in an APS patient. Enriched B cell population from an APS patient, specific to β2GPI, was assayed for antibody secretion following treatment with different concentrations of inhibitory peptides A, B, C, and control peptide D. Irrelevant anti-DNA AFC were used as negative control.

DETAILED DESCRIPTION OF THE INVENTION

Figure 1A:
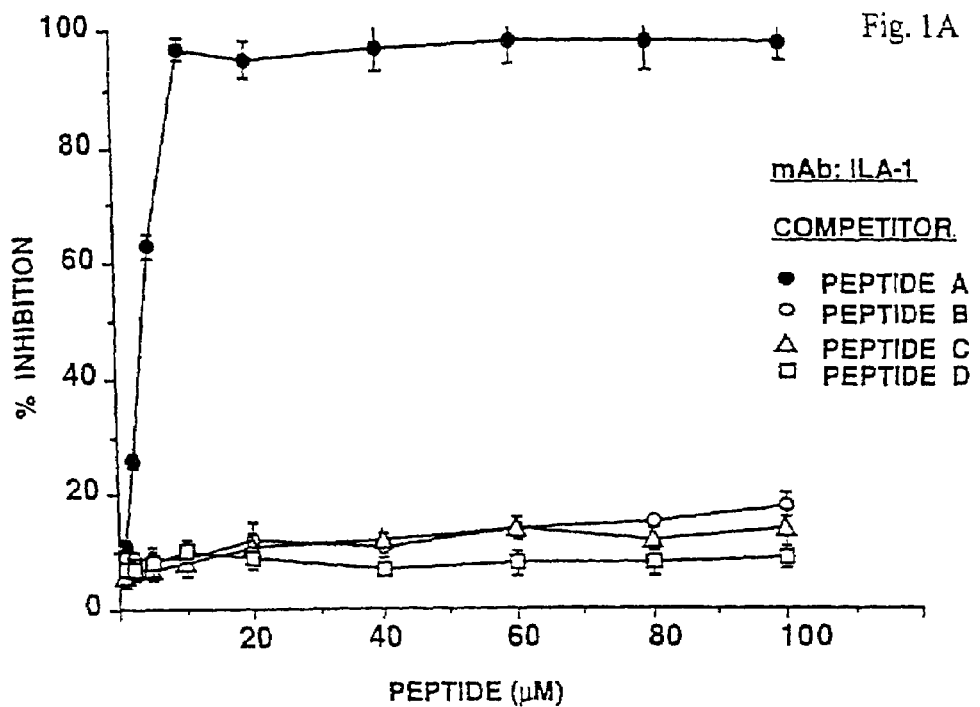
FIGS. 1A–1C are graphs showing inhibition of the anti-β2GPI ILA-1, ILA-3 and G-3 mAbs binding to β2GPI by competition assays using increasing concentrations of the inhibitory monomer peptides A, B and C, respectively, and of unrelated peptide D as control. The percent of inhibition was calculated as follows: % inhibition=O.D control–O.D with inhibitor/O.D control×100. Each point represents mean±SD of three different experiments.

As used herein, the term "peptide derivative" includes a cyclic derivative thereof, an analog in which one or more amino acid residues have been replaced by the corresponding D-isomer or by a non-natural amino acid residue, or a chemical derivative thereof.

The term "cyclic peptide" as used herein refers to cyclic derivatives of a peptide to which two additional amino acid residues suitable for cyclization have been added, one at the carboxyl terminus and one at the amino terminus. Thus, the cyclic peptides contain either an intramolecular disulfide bond, i.e. —S—S—, an intramolecular amide bond between the two added residues i.e.—CONH— or —NHCO—, or intramolecular S-alkyl bonds, i.e.—S—$(CH_2)_n$—CONH— or NHCO—$(CH_2)_n$—S—, wherein n is 1 or 2.

The cyclic derivatives containing an intramolecular disulfide bond may be prepared by conventional solid phase synthesis (Merrifield et al., 1982) while incorporating suitable S-protected cysteine or homocysteine residues at the positions selected for cyclization such as the amino and carboxyl termini (Sahm et al., 1996). Following completion of the chain assembly, cyclization can be performed either by selective removal of the S-protecting groups with a consequent on-support oxidation of free corresponding two SH-functions, to form S—S bonds, followed by conventional removal of the product from the support and appropriate purification procedure, or by removal of the peptide from the support along with complete side-chain deprotection, followed by oxidation of the free SH-functions in highly dilute aqueous solution.

The cyclic derivatives containing an intramolecular amide bond may be prepared by conventional solid phase synthesis while incorporating suitable amino and carboxyl side-chain protected amino acid derivatives at the positions selected for cyclization. The cyclic derivatives containing intramolecular —S-alkyl bonds can be prepared by conventional solid phase synthesis while incorporating an amino acid residue with a suitable amino-protected side chain, and a suitable S-protected cysteine or homocysteine residue at the positions selected for cyclization.

A peptide may have one or more of the amino acid residues replaced by the corresponding D-amino acid residue. Thus the peptide or peptide derivative may be all-L, all-D or a D,L-peptide. In another embodiment, an amino acid residue may be replaced by a non-natural amino acid residue. Examples of non-naturally occurring amino acids include Nα-methyl amino acids, Cα-methyl amino acids, β-methyl amino acids and amino acid analogs in general such as, but not being limited to, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (Orn), hydroxyproline (Hyp), sarcosine, citrulline, cysteic acid, and cyclohexylalanine.

A chemical derivative of a peptide includes, but is not limited to, a derivative containing additional chemical moieties not normally a part of the peptide provided that the derivative retains the inhibitory activity of the peptide. Examples of such derivatives are: (a) N-acyl derivatives of the amino terminal or of another free amino group, wherein the acyl group may be either an alkanoyl group such as acetyl, hexanoyl, octanoyl; an aroyl group, e.g., benzoyl, or biotinyl; (b) esters of the carboxyl terminal or of another free carboxyl or hydroxy groups; and (c) amides of the carboxyl terminal or of another free carboxyl groups produced by reaction with amonia or with a suitable amine.

The multichain peptide-oligomer/polymer conjugate preferably contains two or more identical or different peptides or peptide derivatives attached to an oligomeric or polymeric backbone wherein each of said peptides was identified first to bind to an autoantibody derived from an APS patient and to inhibit the activity of said autoantibody in vitro and in vivo in experimental animals. A multichain peptide conjugate containing a number of different peptides might be preferred.

The peptide or peptide derivative residues can be attached to an oligomer or polymer backbone by any suitable known procedure such as by chemical coupling of the peptide with a water-soluble carbodiimide, e.g. DCC, and then performing the conjugation with the polymer or oligomer by known techniques (Muller et al, 1982).

The multiple antigenic peptide (MAP) system is based on a small immunogenically inert core molecule of radially branching diamino alkanoic acid, preferably lysine, dendrites onto which a number of peptide antigens are anchored (Tam, 1988 and 1989; Posnett et al., 1989). The thus resulting large macromolecule has an unique three-dimensional configuration with a high molar ratio of peptide antigen to core molecule. The MAPs are prepared by standard solid-phase peptide synthesis whereby the inert MAP core, e.g. lysine, is attached to a solid-phase peptide synthesis support, preferably via a spacer, and the desired peptide antigens are synthesized directly on the branched-lysine core. After the synthesis is complete the MAP macromolecule is cleaved from the support using standard techniques. MAP core molecules attached to several different resin supports are commercially available for use in most automated peptide synthesizers. Both Boc- and Fmoc-strategies can be employed with little or no variation of the standard protocols. The crude cleavage products can be obtained by desalting using a Sephadex column.

The spacer in the MAP can be any aminocarboxylic acid including, but not being limited to, aminohexanoic acid and amino acids such as glycine and alanine, or peptides.

According to this embodiment MAPs have been prepared according to the invention with one lysine core onto which two peptide molecules were anchored (herein "divalent" peptides) and with two-lysine core onto which four peptide molecules were anchored (herein "tetravalent" peptides), and the spacer was alanine.

Examples of divalent peptides with peptides derived from monopeptides A–C of the invention and irrelevant peptide D are as follows:

A: Asn Thr Leu Lys Thr Pro Arg Val Gly Gly X Ala (SEQ ID NO:8)

B: Lys Asp Lys Ala Thr Phe Gly Thr His Asp Gly Gly X Ala (SEQ ID NO:9)

C: Cys Ala Thr Leu Arg Val Tyr Lys Gly Gly Gly X Ala (SEQ ID NO:10)

D: Pro Val Arg Ser Pro His Gln Ser Tyr Pro Gly Gly Gly X Ala (SEQ ID NO:11)

wherein X=FmocLys(Fmoc)-OH

Examples of tetravalent peptides with peptides derived from monopeptides A–C of the invention and irrelevant peptide D are as above except for an additional X residue between the X and the Ala residues at the C-terminus.

The peptides of the invention, including the multichain and the multivalent peptides, will be given to patients in a form that insures their bioavailability, making them suitable for treatment. If more than one peptide is found to have significantly inhibitory activity, these peptides will be given to patients in a formulation containing a mixture of the peptides or different peptides are attached to the oligomer or polymer backbone or are anchored onto to the (poly)lysine core.

The invention further includes pharmaceutical compositions comprising at least one synthetic peptide, a derivative thereof, a multichain or multiple antigen peptide according to the invention optionally with a pharmaceutically acceptable carrier.

Any suitable route of administration is encompassed by the invention, including oral, intravenous, subcutaneous, intraarticular, intramuscular, inhalation, intranasal, intrathecal, intraperitoneal, intradermal, transdermal, or other known routes, including the enteral route.

The dose ranges for the administration of the compositions of the present invention should be large enough to produce the desired effect, whereby, for example, production of the pathogenic autoantibodies and their biologic activity are substantially prevented or inhibited, and further, where the disease is significantly treated. The doses should not be so large as to cause adverse side effects, such as unwanted cross reactions, generalized immunosuppression, anaphylactic reactions and the like. The dosage administered will be dependent upon the age, sex, health, and weight of the recipient, kind of concurrent treatment, if any, frequency of treatment, and the nature of the effect desired.

The invention further provides diagnostic kits comprising one or more peptides of the invention and, possibly, other anti-β2GPI mAb inhibitory peptides. Detection of the autoantibodies in serum of the patients may be carried out with the biotinylated peptides using streptavidin-coated ELISA plates, for example, as described in Example 6 herein.

The invention will now be illustrated by the following non-limitative Examples.

EXAMPLES

Materials and Methods (a) Epitope Library. The hexapeptide epitope library was kindly provided by George P. Smith (University of Missouri, Columbia, MO) and was constructed by use of the phage fd-derived vector fUSE5 as described (Scott and Smith, 1990). This library consists of $2\times10^8$ original phage clones each containing a hexapeptide fused to the minor coat protein PIII (Scott and Smith, 1990).

(b) Anti-β2GPI mAbs. The human anti-β2GPI mAbs named ILA-1, ILA-3 and G-3 (IgM), were prepared by human-human hybridoma technique from PBL of an APS patient as described (George et al., 1998). Briefly, peripheral blood cells (PBL) were separated from whole blood by Ficoll-Hypaque gradient, the PBL were exposed to pokeweed mitogen for 5 days in order to enrich the B cell population and the lymphocytes were fused with the human lymphoblastoid cell line GM4672 in the presence of polyethyleneglycol (PEG 1500). After fusion, the cells were seeded into 96-well tissue culture plates with RPMI 1640, 10% FCS and hypoxanthine-aminopterin-thymidine (HAT) selection media. New clones were detected after 4–5 weeks, grown and screened for binding to β2GPI by ELISA. All clones were subjected 4 times to limiting dilution cloning procedures in regular medium. All of the anti-β2GPI mAbs were found to activate endothelial cells in vitro and to induce experimental APS by passive transfer (George et al., 1998).

(c) Identification of peptides which bind specifically to the anti-β2GPI mAbs. The hexapeptide epitope library of section (a) above was used as described (Scott and Smith, 1990). Briefly, a library sample containing $3.8\times10^9$ infectious phage particles was subjected to three rounds of selection (panning) and amplification. For each selection cycle a biotinylated mAb prepared as described in section (b) above (10 μg in the first panning and 1 μg for the others) was added in a total volume of 50 μl. The phages were preincubated with the biotinylated mAb overnight at 4° C., and the reaction mixtures were then layered in 1 ml PBS on streptavidin-coated 30-mm polystyrene petri dishes (Nunc, Kamstrup, Roskilde, Denmark) for 30 min at room temperature. Unbound phages were removed by extensive washings in PBS, and the remaining phages were eluted with 0.1M glycine-HCl, pH 2.2, and neutralized with Tris 1M. Eluted phages were amplified in *Escherichia coli* K91 and used as input in the subsequent round of selection. After three rounds of panning, individual bacterial colonies containing amplified phage clones were grown in microtiter plates overnight at 37° C., and the phages were tested by ELISA for their ability to specifically bind the mAb.

(c)(i) Anti-β2GPI mAb Binding to the Isolated Phages: ELISA plates (Maxisorb, Nunc, Kamstrup, Roskilde, Denmark) were coated with affinity purified rabbit anti-phage M13 (10 μg/ml 0.1M NaHCO$_3$, pH 8.6). Following blocking with 1% gelatin, enriched phage clones, containing $10^9$ phage particles, were then added to the wells and incubated for 1 hour at 37° C. Wells were blocked with 1% gelatin and incubated with the investigated anti-β2GPI mAb (1 μg/ml) overnight at 4° C. The binding of the antibody to the immobilized phage was probed with streptavidin alkaline phosphatase (Jackson Immunoresearch Laboratories Inc, West Grove, Pa., US), and appropriate substrate at O.D. 405 nm. Between each step extensive washings were performed.

(c)(ii) Sequencing: Positive phage clones were propagated and their DNA was sequenced in the epitope region by using a Sequenase version 2.0 kit (United States Biochemical) and the fUSE sequencing primer according to the manufacturer's instructions.

(d) Peptide Synthesis:

(d)(i) General peptide synthesis. All protected amino acids, coupling reagents and polymers were obtained from either Novabiochem AG (Läufelfingen, Switzerland) or Sygena Ltd. (Liestal, Switzerland). Synthesis grade solvents were obtained from Labscan (Dublin, Ireland). Peptides were prepared by conventional solid phase peptide synthesis, using an ABIMED AMS-422 automated solid-phase multiple peptide synthesizer (Langenfeld, Germany). The 9-fluorenylmethoxy-carbonyl (Fmoc) strategy was used throughout peptide chain assembly, following the company's commercial protocols. In each reaction vessel, Wang resin, which contained the first, covalently bound, corresponding N-Fmoc C-terminal amino acid (12.5 μmol) was used (typically, polymer loading of 0.3–0.7 mmol/g resin were employed). Side chain protecting groups were: tert-butyloxycarbonyl (t-Boc) for Lys, tert-butyl-ester (O-t-But) for Asp, tert-butyl-ether (t-But) for Tyr. Ser and Thr, Trityl (Trt) for Asn Gln, His and Cys, and 2,2,4,6,7-pentamethyl-dihydrobenzofuran-5-sulfonyl (PbF) for Arg. Each coupling reaction was performed twice, as a rule, using two successive reactions with 50 μmol (4 eqv) of corresponding N-Fmoc-protected amino acid, 50 μmol (4 eqv) of benzotriazol-1-yl-oxy-tris-pyrrolidino-phosphonium hexafluorophosphate (PyBop) reagent, and 100μmol (8 eqv) of 4-N-methyl-morpholine (NMM), all dissolved in dimethylformamide (DMF), typically for 20–45 min at room temperature. Cleavage of the peptide from the polymer was achieved by reacting the resin with trifluoroacetic acid (TFA)/H$_2$O/triethylsilane (TES); 90:5:5; v/v, for 2 hours at room temperature. The cleavage mixtures were cooled at 4° C., the peptides were precipitated with ice-cold di-tert-butylether (DTBE) and centrifuged for 15 min., 3000 rpm at 4° C. The pellet was washed and centrifuged 3× with DTBE, dissolved in 30% acetonitrile in H$_2$O and lyophilized. The product obtained from each column was analyzed by HPLC. Following analysis, the products were combined, redissolved in 30% acetonitrile in H$_2$O and lyophilized.

(d)(ii) Synthesis of multiple antigenic peptides (MAP). The synthesis of divalent and tetravalent derivatives of peptides A, B, C and D was performed using an ABIMED AMS-42 synthesizer following exactly the protocols described above in section (d)(i). Peptide chain assembly started from Fmoc-Ala-Wang resin. For the preparation of divalent peptides, the second coupling step was achieved with $N^\alpha{}_1N^\epsilon$-Fmoc$_2$-Lys. Removal of Fmoc-protection yielded two amino functions that were extended, each, by two or three Gly residues, according to the desired sequence, and then by the corresponding requisite Fmoc-amino acids. For the preparation of tetravalent peptides, the third coupling step was performed with $N^\alpha{}_1$, $N^\epsilon$-Fmoc$_2$-Lys followed by removal of Fmoc and exposure of four amino functions available for chain extension. Processing of peptide-polymer conjugates and isolation of products were exactly as described above in section (d)(i).

(d)(iii) Biotinylation of peptides and conjugation to streptavidin. Resin-bound peptide (Wang-resin, Calbiochem-Novabiochem AG; Läufelfingen, Switzerland), 11 mg, was suspended in a minimal volume of N-methyl-2-pyrrolidone (NMP). Biotin-N-hydroxysuccinimide (Sigma), 15 μmol, and 15 μmol diisopropylethylamine were added. After 16 hours, the reaction products were washed with NMP, methanol, and ether. The biotinylated peptide was deprotected and cleaved from the resin with a cleavage mixture containing 5% triethylsilan (Fluka Chemicals, Buchs, Switzerland), 5% water, and 90% trifluoroacetic acid. The cleaved peptide was precipitated with ice-cold peroxide-free ether and the pellet was dissolved in water and subsequently lyophilized. The degree of biotinylation was estimated by HPLC and by an optical test based on binding of 2-(4-hydroxyazobenzene) benzoic acid to biotin (Green, 1965). Yields are usually in the range of 40–90%. Purification of biotinylated peptides was achieved by HPLC.

Conjugation to streptavidin: equal volumes of 50 μM streptavidin reconstituted in RPMI and 200 μM biotinylated peptide monomers were mixed at room temperature over 30 min, thus producing a tetramer of four peptide molecules conjugated to a streptavidin molecule.

(d)(iv) Reversed phase HPLC: Analysis of synthetic peptides. For purity determination, analytical reversed-phase HLPC was performed using a prepacked Lichrospher-100 RP-18 column (4×25 mm, 5 μm bead size) employing a binary gradient formed from 0.1% TFA in H$_2$O and with 0.1% TFA in 75% acetonitrile in H$_2$O. All the analyses were performed using a Spectra-Physics SP8800 liquid chromatography system equipped with an Applied Biosystems 757 variable wavelength absorbance detector. The column effluents were monitored by UV absorbance at 220 nm and chromatograms were recorded on a Chrome-Jet integrator. All solvents and HPLC columns were obtained from Merck (Darmstadt, Germany).

(d)(v) HPLC purification of crude peptides was achieved employing semi-preparative column (Merck; 250×10 mm; 7 μm) with the above gradient. The following peptides were synthesized: peptides A, B, C and D as monomers, dimers and tetramers thereof with streptavidin, and divalent and tetravalent MAPs thereof with Lys.

(d)(vi) Amino acid composition analysis. Peptide solutions were roto-evaporated (about 40 μg of peptide in 40 μl solution with 5 μg of norvaline as an unnatural amino acid internal standard), hydrolyzed in 6N HCl at 110° C. for 22 hours under vacuum and analyzed with a HP 1090 amino acid analyzer, using on-line pre-column ortho-phthalaldehyde (OPA)/Fmoc derivatization combined with reversed-plase chromatography. This quantification was used as a basis for determining the total peptide yield.

(e) Inhibition of anti-β2GPI mAb binding to β2GPI by the inhibitory peptides. For competition ELISA tests, the anti-β2GPI mAbs (10 μg/ml) were preincubated (overnight at 4° C.) with varying concentrations of the peptides. The competition reaction was then transferred to β2GPI-coated γ-irradiated ELISA plates (Nunc), and the assay continued as described above. The percentage of inhibition was calculated as follows: % inhibition=O.D control −O.D with inhibitor/O.D control×100.

(f) Anti-β2GPI mAb binding to endothelial cells in the presence of the inhibitory peptides. Human umbilical vein endothelial cells (HUVEC) were isolated as previously described and cultured under standard conditions (Jaffe et al., 1973). Briefly, umbilical cords were treated with collagenase (0.2% from *Clostridium histolyticum*, Boehringer) for 20 min at 37° C., cells were cultured in medium 199 with 20% FCS, 10 μg/ml growth supplement, 100 μg/ml heparin and antibiotics (streptomycin, penicillin), and used at passages 1–2 for plating onto gelatin-coated 96-well plates. Cyto-ELISA was performed as detailed before (Jaffe et al., 1973). Briefly, mAbs at different concentrations were added to HUVEC confluent wells, previously coated with 10 μg/ml β2GPI for 2 hours and fixed with 0.1% glutaraldehyde. The bound mAb was detected by further 1-hour incubation with alkaline phosphatase-conjugated goat anti-human IgM.

(g) Adherence of U937 monocyte cells to endothelial cells in the presence of anti-β2GPI mAbs and the inhibitory peptides. This assay was performed as previously described (Carvalho et al., 1996). Briefly, U937 cells (a monocyte/macrophage-like cell line) were pretreated with heat-aggregated gamma-globulin for 30 min at 37° C. (to block Fc receptor binding) and labeled with 0.1 μCi/ml of [$^3$H]-thymidine (Amersham International, Little Chalfont, UK) for 24 hours. Adhesion assays were performed on HUVEC monolayers which were preincubated with β2GPI and mAbs, with and without different concentrations of specific and irrelevant peptides, overnight. The endothelial cell (EC) monolayers were extensively washed, and radiolabeled U937 cells were added to each well, in RPMI 1640 medium containing 0.2% BSA for 30 min at 37° C. The nonadherent cells were removed by washing and the cells were lysed with formic acid. Radioactivity associated with adherence was quantified by beta-scintillation spectroscopy. The results were expressed as percent of added U937 cells that adhered and are presented as the mean±SD from 3–5 replicate wells.

(h) ELISA for detecting the expression of adhesion molecules following exposure to anti-β2GPI mAbs and the inhibitory peptides. HUVEC cells grown in 96-well plates and preincubated with mAbs, with and without different concentrations of specific and irrelevant peptides (100 ug/ml), were washed, fixed with 0.1% glutaraldehyde, and then treated with PBS containing 0.2% Triton-X100 in order to permeabilize the cell membrane (Adamson et al., 1996). The plates were blocked with 3% BSA and incubated with biotinylated mouse anti-human E-selectin, anti-human intracellular adhesion molecule-1 (ICAM-1) or anti-human vascular cell adhesion molecule-1 (VCAM-1) (PharMingen, Torreyana Road, San Diego, Calif.) 1 μg/ml for 1 hour. The cells were then exposed to streptavidin alkaline phosphatase (Jackson) and appropriate substrate.

(i) Mice: Female BALB/c mice, aged 10–12 weeks, were purchased from Tel-Aviv University Animal House, Israel. The females were caged overnight with BALB/c males and examined for vaginal plug next morning. The presence of the plug was considered as day 0 of pregnancy in all the studied groups.

(j) Induction of murine experimental APS. Mice were infused intravenously with 20 μg of each one of the anti-β2GPI ILA-1, ILA-3, and G-3 mAbs at day 0 (the day at which a vaginal plug was observed following mating) (Blank et al., 1991), 6 hours later the mice received daily 40 μg/mouse of the tested peptides during 3 days. The mice were bled and sacrificed on day 15 of pregnancy. Fetal resorptions, activated partial thromboplastin time and platelet counts (markers of the APS-equivalent in mice) were determined as described (Blank et al., 1991).

(k) Anti-β2GPI antibody secretion by hybridoma cells in the presence of the inhibitory peptides. Hybridoma cells named ILA-1, ILA-3, and G-3 were tested for secretion of anti-β2GPI mAbs following 48 h of treatment with specific inhibitory monomer peptides A, B or C, their dimers and tetramers with St, or the corresponding divalent and tetravalent peptides. PE hybridoma cells secreting irrelevant immunoglobulin were used as negative control. The hybridoma cultures were washed after 48 h and incubated for 5 more days. Culture fluid was tested for the presence of anti-β2GPI mAbs by ELISA.

(l) Anti-β2GPI Abs secretion from PBL of APS patients in the presence of the inhibitory peptides. PBL separated from APS patient blood on Ficoll-Hypaque gradient (Pharmacia) were incubated for 48 h with specific inhibitory monomer peptides A, B or C, or the corresponding divalent and tetravalent peptides, at concentration of 10 μM, added daily. The PBL cultures were washed 48 h later and incubated for 5 more days. Culture fluid was tested for the presence of anti-β2GPI IgM and IgG Abs by ELISA.

(m) Detection of human anti-β2GPI Ab secreting B cells in PBL population from APS patient following exposure to the inhibitory peptides. PBL were separated on Ficoll-Hypaque gradient (Pharmacia), loaded on an anti-CD19 microbead column, followed by streptavidin-microbeads coated with biotinylated β2GPI. The thus affinity purified B cells were assayed for their ability to secrete in vitro anti-β2GPI Abs. The B cells were incubated for 24 h with the inhibitory peptides A, B or C, or with irrelevant peptide D, as monomers or as divalent and tetravalent MAPs, at different concentrations. The enriched population of total B cells ($1\times10^6$/ml) were seeded in RPMI 1640 medium in the presence of 10% FCS onto 24-well tissue culture plates (Nunc) precoated with β2GPI (10 μg/ml), or DNA (as negative control) (10 μg/ml), and blocked with gelatin. The plates were incubated overnight at 37° C. in an atmosphere of 7% $CO_2$. Following extensive washings, anti-human IgG or IgM conjugated to alkaline phosphatase was added for 2 h at 37° C. Spots of immunoglobulin secreted by each B cell were probed by adding the substrate BCIP (Sigma) in 2-aminopropranolol Triton X-405 $MgCl_2$ buffer to 3% agar (type I, low electroendosis; Sigma) heated and diluted in BCIP buffer at 4:1 ratio, resulting in a 0.6% agar solution. ELISPOTS (blue spots) were evaluated after exposure of the cells to specific and non-specific peptides.

(n) Statistical analysis: ANOVA statistical analysis was used to evaluate differences between the binding properties and the biological activity of the various studied groups. $p<0.05$ was considered as statistically significant.

Example 1

Isolation of Peptide-Presenting Phases Binding Specifically to Anti-β2GPI mAbs

The anti-β2GPI mAbs ILA-1, ILA-3 and G-3 were subjected to a phage library containing random hexapeptides to determine peptide sequences which are recognized by them, as described in Materials and Methods, section (c). Three rounds of selection were performed, and selected phages were randomly chosen for sequencing after the third round. The different sequences in phages, probed by the biotinylated mAbs, are summarized in Table 1.

TABLE 1

Binding of anti-β2GPI mAbs to phage isolated from an hexapeptide epitope library

| Antibody | Epitope sequence* | SEQ ID NO: | Binding O.D. | Phages identified, no. |
|---|---|---|---|---|
| ILA-1 | L K T P R V | 8 (res. 3–8) | 975 ± 72 | 24 |
|  | K T P R V T | 12 | 1201 ± 142 | 18 |
| ILA-3 | K D K A T F | 13 | 1178 ± 101 | 15 |
| G-3 | T L R V Y K | 14 | 791 ± 33 | 12 |
|  | T K L R V Y | 15 | 954 ± 62 | 7 |
|  | T L L R V Y | 16 | 869 ± 71 | 16 |

Binding of anti-β2GPI mAbs 5 μg/ml, to $10^9$ phage particles/well, by ELISA (O.D. at 405 nm). Binding of ILA-1 to irrelevant hexapeptide PVRSPH resulted in O.D. of 92 ± 11.
*Amino acid sequence (deduced from DNA sequence) of the inserted hexapeptide.

ILA-1 mAb detected the sequence KTPRV (residues 4–8 of SEQ ID NO:8) that appeared in 42 clones, wherefrom 24 clones showed the sequence LKTPRV (residues 3–8 of SEQ ID NO:8) which represents a mimotope located between domain I/II of the β2GPI molecule as LK(C)TPRV (SEQ ID NO:17) on the native form of the β2GPI. The other 18 clones showed the motif KTPRVT (SEQ ID NO12) presented at the same location on the β2GPI and appearing as K(C)TPRV (CC)T (SEQ ID NO:18).

ILA-3 mAb fished out the linear sequence KDKATF (SEQ ID NO:13) located on the fourth domain of the β2GPI molecule (15 clones). ILA-4 mAb probed the sequence mimotope LVEPWR (SEQ ID NO:19) the location of which on β2GPI is still undetermined. The anti-β2GPI mAb named G-3 recognized a linear motif sequence LRVY (residues 3–6 of SEQ ID NO:15) located on the third domain of the β2GPI molecule, that appeared in 37 of the examined clones.

Example 2

Inhibition of Binding of Anti-β2GPI mAbs to β2GPI and to Endothelial Cells by the Synthetic Monomer Peptides A, B and C (2a) The specificity of interaction of the mAbs with the corresponding synthetic peptides A, B, C and control peptide D as monomers, was assessed by inhibition experiments as described in Materials and Methods, sections (e) and (f).

Figure 1B:
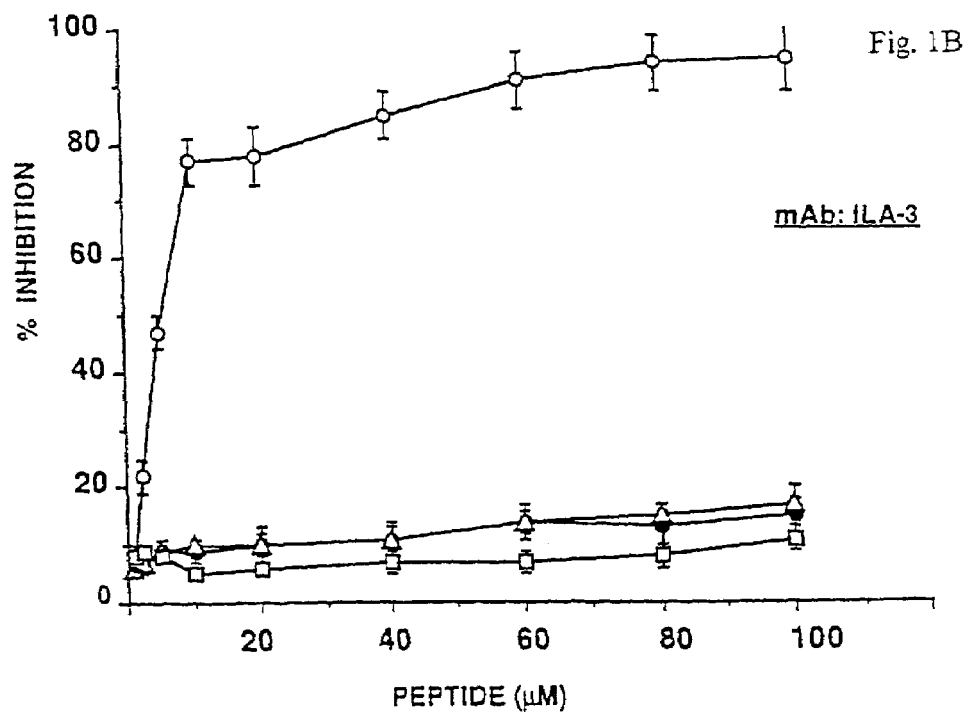
Figure 1C:
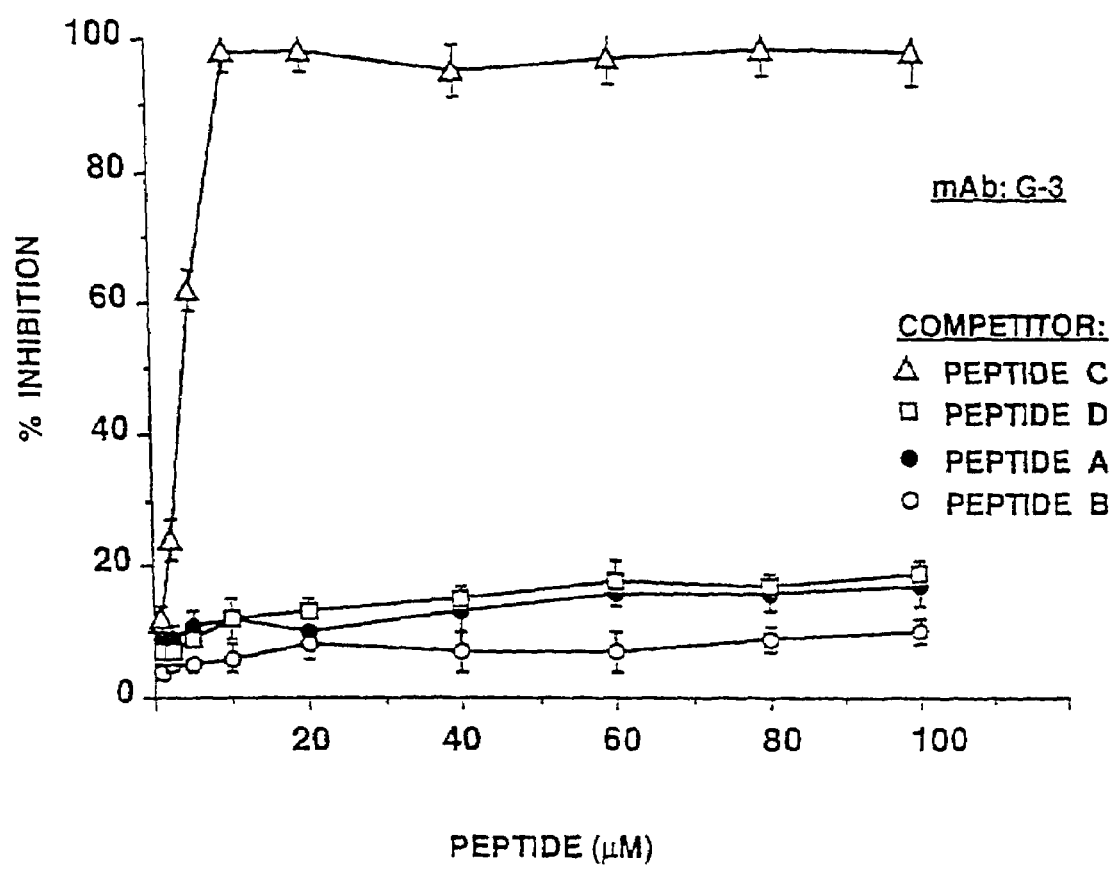

The results depicted in FIG. 1A show that peptide A (filled circles) inhibited ILA-1 mAb binding to β2GPI by 97% at 10 μM peptide concentration, while peptides B and C, directed to other locations on the β2GPI molecule, as well as irrelevant peptide D (open circles, open triangles and open squares, respectively) did not have any inhibitory effect (10%, 11% and 8%, respectively), at the same peptide concentration. Peptide B abrogated the binding of ILA-3 mAb to β2GPI by 77% (FIG. 1B, open circles), and 98% inhibition of G-3 mAb binding to β2GPI was exhibited by peptide C (FIG. 1C, open triangles), both at 10 μM peptide concentration. The specificity of the inhibition of binding of ILA-3 and H-3 mAbs to β2GPI by the tested peptides was clearly evident when the inhibition assay performed by preincubation of the tested anti-β2GPI mAb with the specific peptide B or C, respectively, was compared to the binding following preincubation with the other tested peptides shown in FIGS. 1B and 1C (peptides A, C, D and A, B, D, respectively).

Figure 2C:
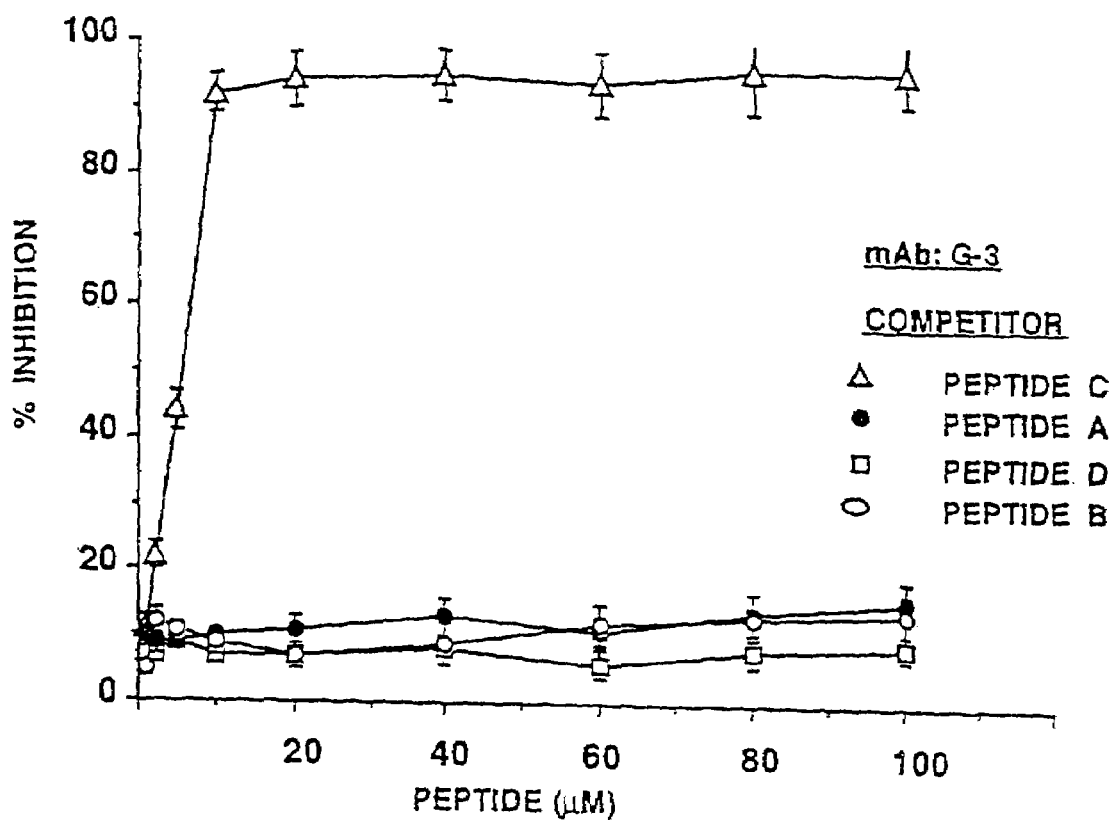

(2b) The anti-β2GPI mAb binding to HUVEC in the presence of peptides A, B, C and D was carried out as described in Materials and Methods, section (f). The specificity of interaction of the anti-β2GPI mAbs corresponding peptides and HUVEC is shown in FIGS. 2A–C. Peptides A, B and C inhibited the binding of ILA-1, ILA-3 and G-3 mAbs to HUVEC by 95% (FIG. 2A, filled circles), 72% (FIG. 2B, open circles), and 92% (FIG. 2C, open triangles), respectively, at peptide concentration of 10 µM. No inhibition of binding of the anti-β2GPI mAbs to HUVEC by peptides directed to other locations on the β2GPI molecule, or by irrelevant peptide D, was observed (FIGS. 2A–C).

Example 3

Peptides which Bind Specifically to anti-β2GPI mAbs have a Preventive Effect on the Ability of the anti-β2GPI mAbs to Enhance Monocyte Adhesion to Endothelial Cells The adhesion of monocytes to endothelial cells (EC) is considered a marker of EC activation. The percentage of adhesion is expressed as the portion of added U937 monocyte cells adhering to the HUVEC (thus reflecting the percentage of HUVEC coverage by the monocytes). The ability of the peptide monomers A, B and C to prevent activation of HUVEC via decrease of the adhesion percentage of U937 monocytes to HUVEC, was tested as described in Materials and Methods, section (g).

Figure 3A:
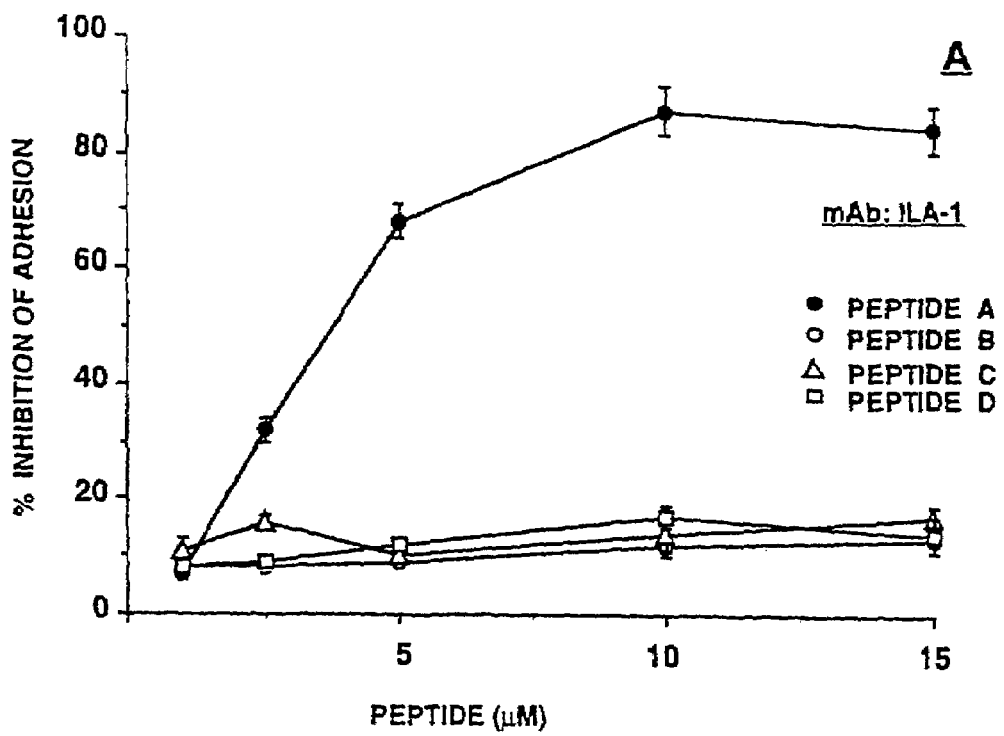
FIGS. 3A–3C are graphs showing inhibition of U937 monocyte cell adhesion to HUVEC upon exposure to anti-β2GPI ILA-1, ILA-3 and G-3 mAbs and increasing concentrations of the inhibitory monomer peptides A, B and C, respectively, and of unrelated peptide D as control. The percentage of inhibition of adhesion was calculated as follows: % inhibition of adhesion=CPM in the presence of anti-β2GPI mAb–CPM in the presence of anti-β2GPI mAb and the tested peptide/CPM in the presence of anti-β2GPI mAb×100 (CPM=counts/min). Each point represents mean±SD of three different experiments.
Figure 3B:
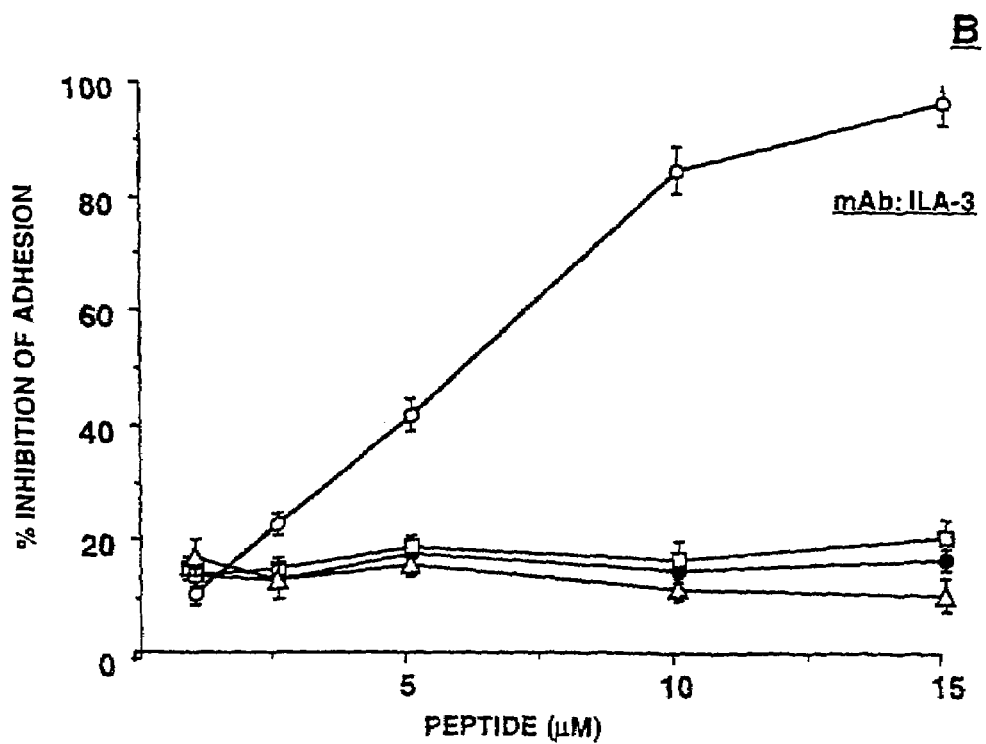
Figure 3C:
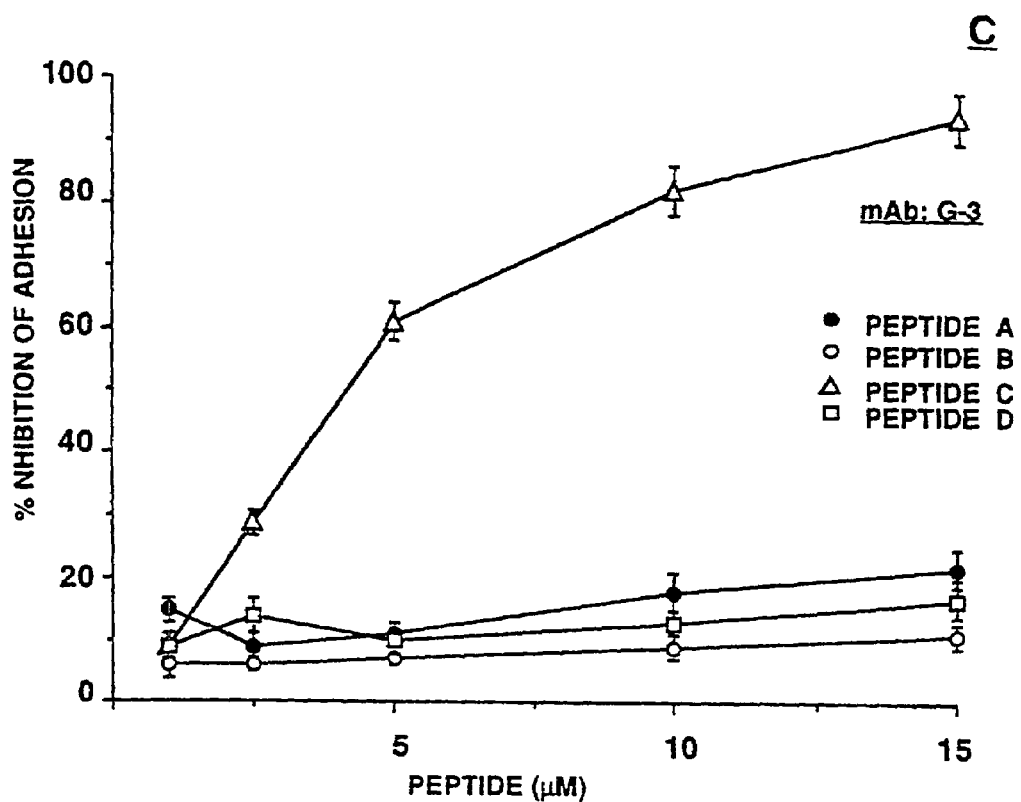

As shown in FIG. 3A, ILA-1 mAb preincubated with peptide A (filled circles) inhibited the adhesion of U937 to HUVEC under the experimental conditions used by 84% at 10 µM peptide concentration, as compared to 6–17% inhibition in the presence of peptides B and C, or of irrelevant peptide D (open circles, open triangles and open squares, respectively). The most significant prevention of adhesion of U937 monocyte cells to HUVEC was accomplished by preincubation of G-3 mAb with peptide C with 92% inhibition, or by preincubation of ILA-3 mAb with peptide B with 95% inhibition, at peptide concentration of 15 µM (FIGS. 3C and 3B, respectively). The specificity of inhibition of adhesion of U937 cells to HUVEC by the inhibitory peptides corresponding to each anti-β2GPI mAb was confirmed, in each case, by using the other peptides specific to different anti-β2GPI mAbs or the irrelevant peptide D, as shown in FIGS. 3B and 3C (7–21% inhibition, at peptide concentration of 10 µM, $p<0.001$).

Example 4

Prevention of Expression of the Adhesion Molecules E-Selectin, ICAM-1 and VCAM-1 on HUVEC by Peptides Directed Specifically to anti-β2GPI mAbs.

Figure 4:
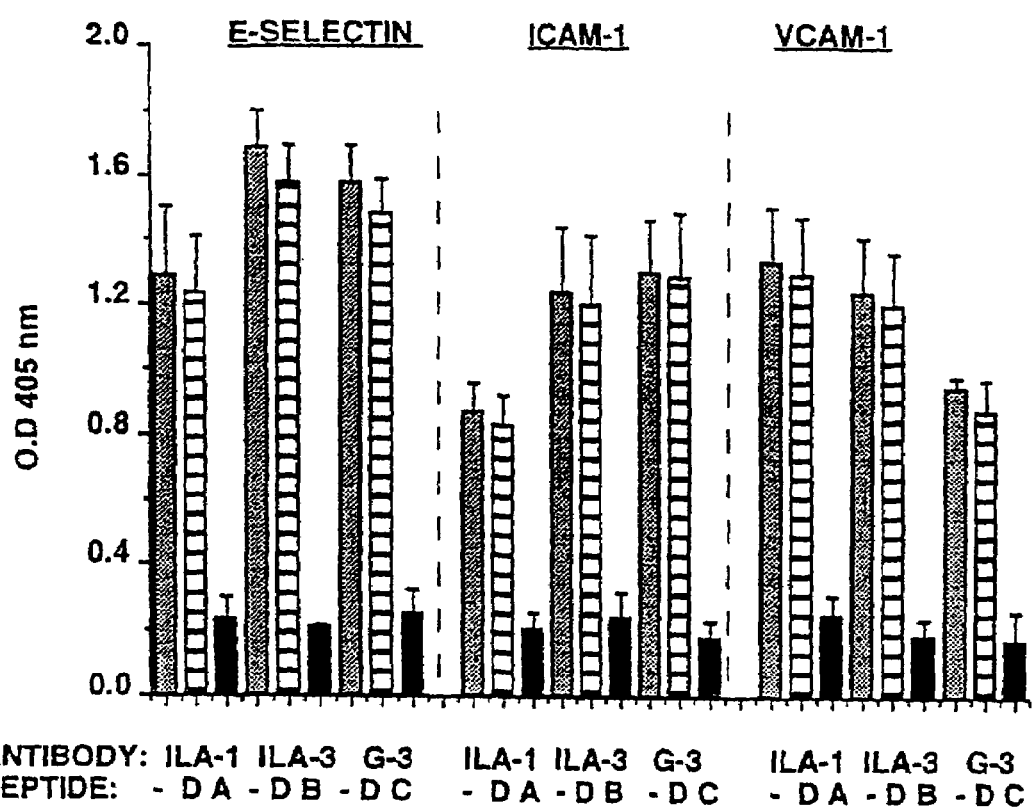
FIG. 4 is a bar graph showing inhibition of expression of the adhesion molecules E-selectin, intracellular adhesion molecule-1 (ICAM-1) and vascular cell adhesion molecule-1 (VCAM-1) on HUVEC by specific inhibitory monomer peptides A, B, or C. To the HUVEC incubated with β2GPI, were added anti-β2GPI ILA-1, ILA-3 and G-3 mAbs with and without preincubation (2 h) with the peptide monomers A, B and C, respectively, and control peptide D. The expression of adhesion molecules was probed by ELISA employing biotinylated anti-human ICAM-1, VCAM-1, E-selectin and streptavidin-alkaline phosphatase. Each point represents mean±SD of three different experiments.

The enhancement of monocytes to endothelial cells followed by increase in the amount of adhesion molecules expression, as a result of exposure of endothelial cells to anti-β2GPI mAbs, has been observed previously at the laboratory of one of the present inventors. The effect of each specific peptide monomer A, B, C on the expression of the adhesion molecules E-selectin, ICAM-1 and VCAM-1 on HUVEC caused by the corresponding anti-β2GPI mAb, was examined according to Materials and Methods, section (h). The results are shown in FIG. 4, in which the black columns represent treatment with a specific peptide (i.e., peptides A, B and C for ILA-1, ILA-3 and G-3 mAbs, respectively), the lined columns represent treatment with a cocktail of non-specific peptides (i.e., peptides B+C+D, A+C+D and A+B+D for ILA-1, ILA-3 and G-3 mAbs, respectively), and the dotted columns correspond to peptide-untreated cells.

The most pronounced inhibitory effect was evident on E-selectin expression by HUVEC following preincubation of peptide B with ILA-3 mAb (O.D. 0.211±0.064 in comparison to OD 1.591±0.137 in the presence of irrelevant peptides A+C+B, $p<0.001$). Peptide B also abrogated the expression of ICAM-1 ($p<0.002$) and VCAM-1 ($p<0.001$) by HUVEC exposed to ILA-3 mAb.

Preincubation of the mAb ILA-1 with peptide A or mAb G-3 with peptide C also resulted in a significant inhibition of E-selectin expression by HUVEC (O.D 0.239±0.064, O.D 0.215±0.047 in comparison to O.D 1.232±0.212, 1.597±0.225, respectively, in the presence of peptide D, $p<0.001$).

Inhibition of ICAM-1 expression was most impressive when G-3 mAb was preincubated with peptide C and added to HUVEC (O.D 0.186±0.062 in comparison to OD 1.315±0.117, $p<0.001$, in the presence of peptide D), compared to ICAM-1 expression following exposure of HUVEC to peptide A and ILA-1mAb (O.D. 0.204±0.072 compared to O.D 0.834±0.056 in the presence of peptide D, $p<0.002$). The comparison between the inhibitory effect of peptides B and C on the adhesion molecules expression by HUVEC caused by ILA-3 and G-3 mAbs, respectively, was non-significant, $p>0.05$.

Inhibition of VCAM-1 expression showed the most significant effect with peptide A and ILA-1 mAb (O.D 0.252±0.071 compared to O.D 1.372±0.203 with the cocktail of irrelevant peptides B+C+D, $p<0.001$). G-3 mAb, which had less pronounced ability to activate VCAM-1 expression on HUVEC (O.D 0.809±0.063 incubation with the cocktail of irrelevant peptides A+B+D, was inhibited by peptide C(O.D 0.174±0.062, $p<0.004$).

Example 5

Prevention of APS Induction in Naive Pregnant Mice by Peptides Specific to anti-β2GPI mAbs.

Significant fetal loss, thrombocytopenia and prolonged activated thromboplastin time (aPTT) were induced in naive mice following passive intravenous administration of the three anti-β2GPI mAbs ILA-1, ILA-3 and G-3, as described in Materials and Methods, section (j). The clinical manifestations of the experimental APS were prevented by infusion of the specific peptide monomers A, B, C which were delivered to the mice with the corresponding pathogenic anti-β2GPI mAbs, as shown in Table 2. The cocktail of irrelevant peptides in each case did not affect the development of the disease symptoms. Similarly, mice which were preinfused with control IgM and received a cocktail of the peptide monomers (A+B+C), were not affected.

BALB/c mice which were preinfused with anti-β2GPI mAb ILA-1, and treated thereafter with peptide monomer A, showed normal values of fetal loss (8±2%) compared to mice which were infused with the irrelevant peptide monomer cocktail (B+C+D) (45±2%), or to non-treated mice (39±3%, $p<0.001$; $p>0.5$) when compared to mice infused with control human IgM that was administered with the peptide cocktail (B+C+D). The platelet count in the peptide A-treated mice was 989±103cells/mm$^3$×10$^3$, which is normal in comparison to mice infused with the human IgM and treated with the peptide cocktail (A+B+C), $p>0.5$. Significancy ($p<0.003$) was observed when the above platelet count was compared to non-treated ILA-1 infused mice (498±142 cells/mm$^3$×10$^3$), or those treated with the peptide cocktail (B+C+D) (532±162 cells/mm$^3$×10$^3$). No prolongation in activated partial thromboplastin time (aPTT) was observed in mice infused with ILA-1 and treated with peptide A (33±4 sec) compared to IgM-infused mice with and without treatment with the peptide cocktail (B+C+D) (31±2, 28±3 sec), $p>0.05$.

The same pattern of preventing effects by the specific peptides was shown in mice infused either with pathogenic anti-β2GPI ILA-3 mAb and treated with peptide monomer B or with pathogenic G-3 mAb and treated with peptide monomer C (Table 2). The values of fetal loss were significantly normal, $p>0.5$, in comparison to IgM-infused mice with and without treatment with the peptide cocktail; $p<0.001$ when compared to ILA-3 or G-3 infused mice treated with the peptide monomer cocktail (A+C+D) or (A+B+D), respectively. No thrombocytopenia was detected in mice infused either with pathogenic anti-β2GPI ILA-3 mAb and treated with peptide B or with G-3 mAb and treated with peptide C, $p>0.5$ in comparison to IgM-infused mice with and without treatment with the peptide cocktail (A+C+D) or (A+B+D), $p<0.002$ and $p<0.001$, respectively, when compared to ILA-3 or G-3 infused mice treated with peptide cocktail (A+C+D) or (A+B+D), respectively. Activated partial thromboplastin time (aPTT) in mice infused with either ILA-3 mAb and treated with peptide B or G-3 mAb and treated with peptide C, was normal (27±2 and 31±4 sec, respectively), $p>0.5$ in comparison to IgM-infused mice with and without treatment with the peptide cocktail; $p<0.002$ when compared to ILA-3 or G-3 infused mice treated with peptide cocktail (A+C+D) or (A+B+D), respectively.

16.3%, respectively, out of 43 APS patients, and in 15.3% and 6.8%, respectively, out of 72 SLE patients.

As shown in Table 4, the percentage of antibodies from the total anti-β2GPI affinity purified Abs (from 25 APS patients) recognizing the inhibitory monomer peptides A, B C, was in the range between 44% to 0.5%.

TABLE 3

Percent of sera from APS and SLE recognizing the inhibitory peptide A, B and C

| | APS patients (N = 43) | | SLE patients (N = 72) | | Normal donors (N = 100) | |
|---|---|---|---|---|---|---|
| | IgG | IgM | IgG | IgM | IgG | IgM |
| Peptide A | 7 | 20.9 | 5.5 | 11 | 0 | 2 |
| Peptide B | 20.9 | 25.6 | 11 | 12.5 | 0 | 1 |

TABLE 2

Clinical manifestations in mice infused with anti-β2GPI mAbs and peptides A, B, C

| Infusion of mAb: | ILA-1 | | | ILA-3 | | | G-3 | | | HIgM | |
|---|---|---|---|---|---|---|---|---|---|---|---|
| Peptide: | A | NON | B + C + D | B | NON | B + C + D | C | NON | B + C + D | NON | A + B + C |
| aPTT(SEC.) @ | 33 ± 4 (p < 0.02)* | 72 ± 5 | 78 ± 3 | 27 ± 2 (p < 0.02)* | 64 ± 3 | 69 ± 3 | 31 ± 4 (p < 0.02)* | 83 ± 5 | 79 ± 4 | 31 ± 2 | 28 ± 3 |
| Platelet count @ (cells/mm³ × 10⁻³) | 989 ± 103 (p < 0.003)* | 498 ± 142 | 532 ± 162 | 1137 ± 219 (p < 0.002)* | 579 ± 163 | 601 ± 134 | 1242 ± 267 (p < 0.001)* | 499 ± 112 | 676 ± 105 | 1189 ± 273 | 1207 ± 212 |
| % Fetal loss | 8 ± 2 (p < 0.001)* | 39 ± 3 | 45 ± 2 | 6 ± 2 (p < 0.001)* | 42 ± 3 | 49 ± 4 | 7 ± 2 (p < 0.001)* | 42 ± 4 | 39 ± 4 | 6 ± 2 | 8 ± 4 |

Values are expressed as mean ± SD of 2 experiments; N = 11–15 mice in each group.
@ aPTT: activated partial thromboplastin time. % Feal loss = Resorbed fetuses/Total fetuses
*Statistical analyses were performed by ANOVA test. Groups of mice treated with peptide A, B or C, were compared to groups of mice treated with cocktail of peptides (B + C + D), (A + C + D) or (A + B + D) respectively.

Example 6

Frequency of anti-β2GPI Target Epitopes A, B and C in Patients with Primary APS or Secondary to SLE Binding of sera from patients with primary APS or secondary to SLE to the studied peptides was performed by ELISA. 96-well ELISA plates were coated with streptavidin, blocked with gelatin, incubated with biotinylated peptides (A,B,C,D) and blocked with gelatin. Sera of patients with APS or SLE were added at dilution of 1:50 and the percent of binding was probed with anti-human IgM or IgG conjugated to alkaline phosphatase. Half plate was coated with streptavidin without addition of peptide (for non-specific binding).

Figure 5:
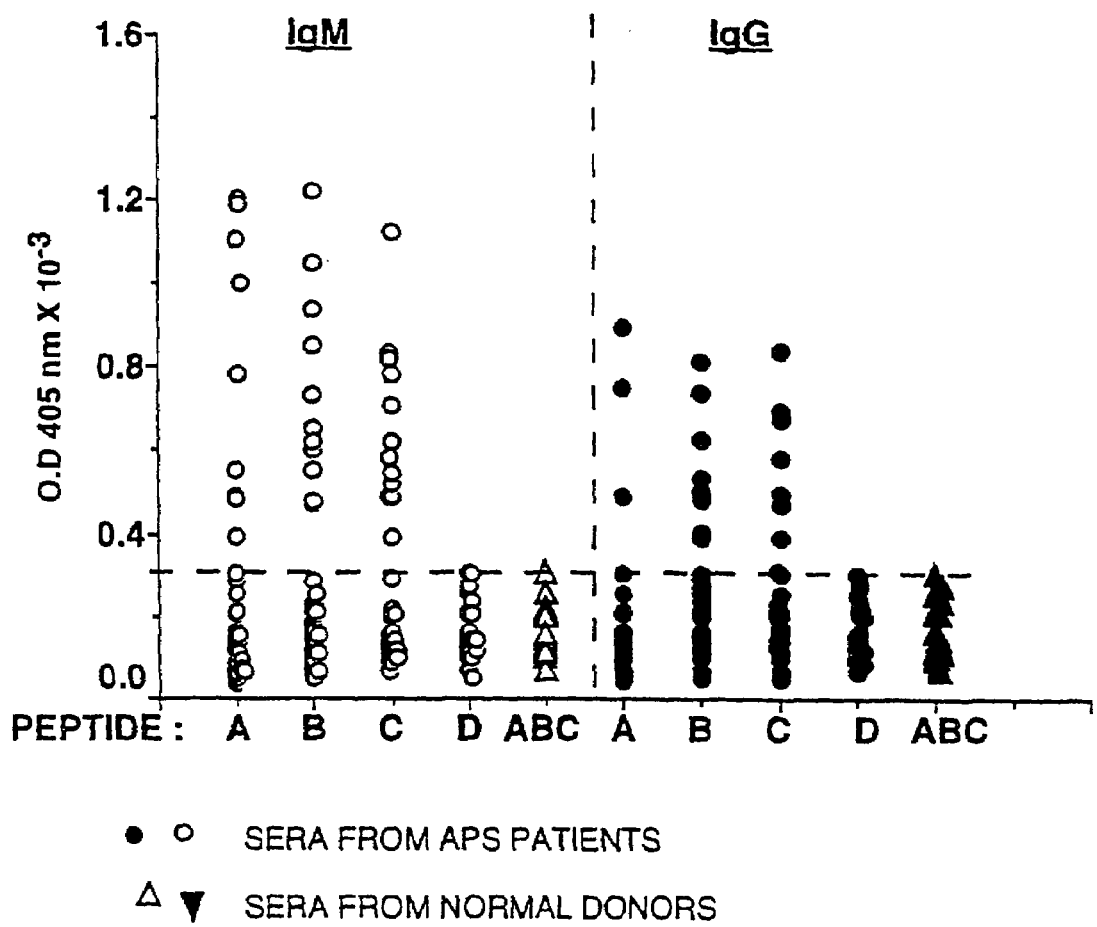
FIG. 5 shows direct binding of sera of APS patients to the inhibitory monomer peptides A, B or C. ELISA streptavidin-coated plates were incubated with biotinylated A, B or C, control peptide D or cocktail of peptides A+B+C. Following blocking with 5% bovine sera, the patient sera were added at dilution of 1:50. The bound antibodies were detected by administration of anti-human IgG or IgM alkaline phosphatase and appropriate substrate.

FIG. 5 shows the direct binding of anti-β2GPI IgM and IgG of APS patients to peptides A, B, C, and D, presented in O.D. at 405 nm. The sera from the APS patients were found to bind differentially the tested peptides, either as a result of distinct affinity to the peptides or due to different titers of antibodies recognizing the target epitopes.

As shown in Table 3, peptide A was recognized by anti-β2GPI IgM and anti-β2GPI IgG in 21% and 7%, respectively, out of 43 APS patients, and in 11% and 5.5%, respectively, out of 72 SLE patients. Peptide B was recognized by anti-β2GPI IgM and anti-β2GPI IgG in 25.6% and 20.9%, respectively, out of 43 APS patients, and in 12.5% and 5.5%, respectively, out of 72 SLE patients. Peptide C was recognized by anti-β2GPI IgM and IgG in 32.5% and TABLE 3-continued Percent of sera from APS and SLE recognizing the inhibitory peptide A, B and C

| | APS patients (N = 43) | | SLE patients (N = 72) | | Normal donors (N = 100) | |
|---|---|---|---|---|---|---|
| | IgG | IgM | IgG | IgM | IgG | IgM |
| Peptide C | 16.3 | 27.9 | 2.8 | 14 | 1 | 0 |
| Peptide D | 0 | 0 | 0 | 0 | 2 | 1 |

N = Number of patients studied

TABLE 4

Fraction of anti-β2GPI Abs (in percentage), recognizing peptide A, B, or C, in each APS patient studied

| Patient no. | PEPTIDE A | PEPTIDE B | PEPTIDE C |
|---|---|---|---|
| 1 | 23 | 37 | 0.4 |
| 2 | 0.7 | 15 | 3 |
| 3 | 1.4 | 0.5 | 39 |
| 4 | 29 | 43 | 22 |
| 5 | 0.9 | 29 | 1.8 |
| 6 | 29 | 14 | 23 |
| 7 | 37 | 18 | 5 |
| 8 | 2.8 | 33 | 4.2 |

TABLE 4-continued

Fraction of anti-β2GPI Abs (in percentage), recognizing peptide A, B, or C, in each APS patient studied

| Patient no. | PEPTIDE A | PEPTIDE B | PEPTIDE C |
|---|---|---|---|
| 9 | 12 | 1.3 | 0.5 |
| 10 | 0.6 | 7.9 | 16.4 |

Affinity purified anti-β2GPI Abs were loaded on peptide A column, eluted and passed through peptide B column followed by peptide C column. The percentage of anti-peptide A, B, and anti-peptide C were calculated from total anti-β2GPI Abs.

Example 7

Specificity of Recognition of the anti-β2GPI Epitopes in Primary APS Patients

Figure 6A:
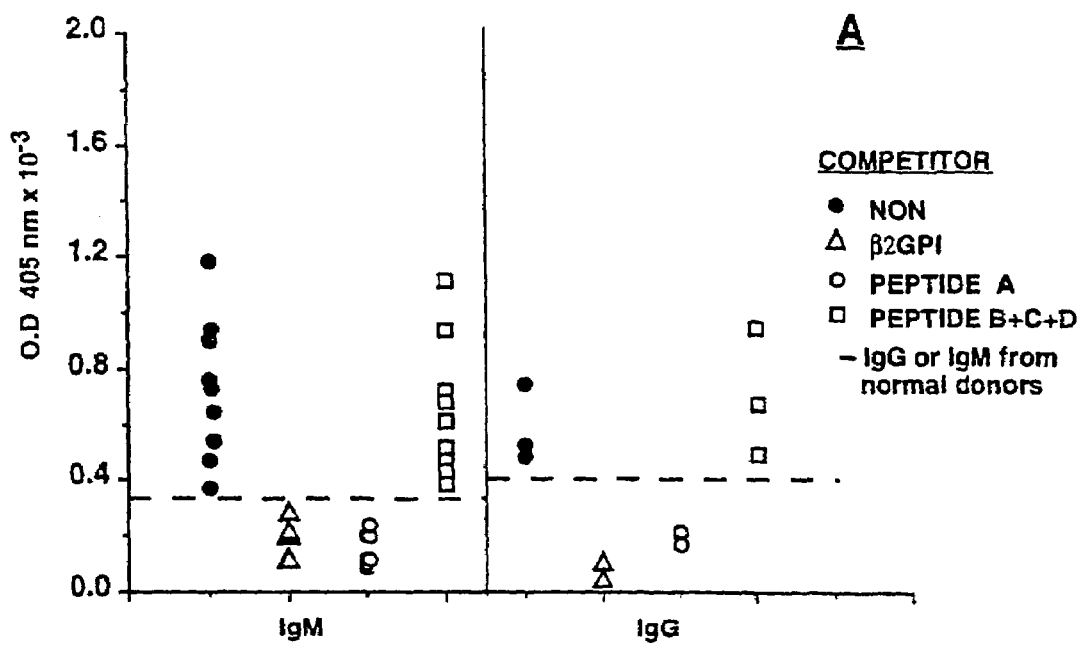
FIGS. 6A–6C show specificity of binding of affinity purified anti-β2GPI IgM and IgG antibodies from APS patients to the inhibitory monomer peptides A, B and C by ELISA, following preincubation of the tested affinity purified immuno-globulin with or without the peptide or the β2GPI molecule, in fluid phase.
Figure 6B:
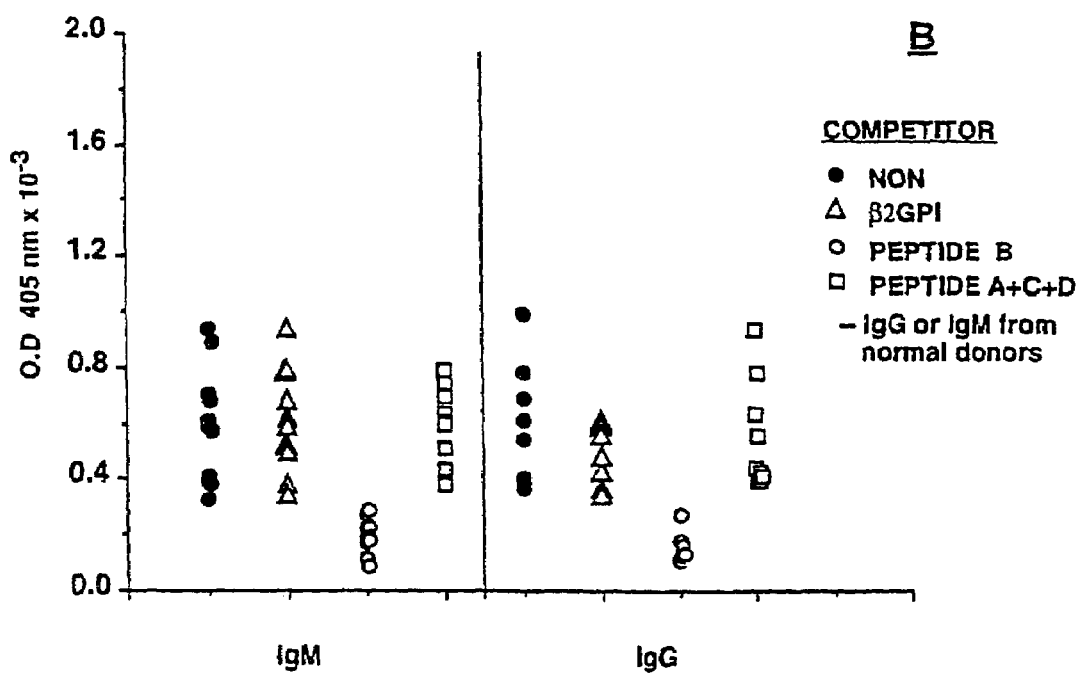
Figure 6C:
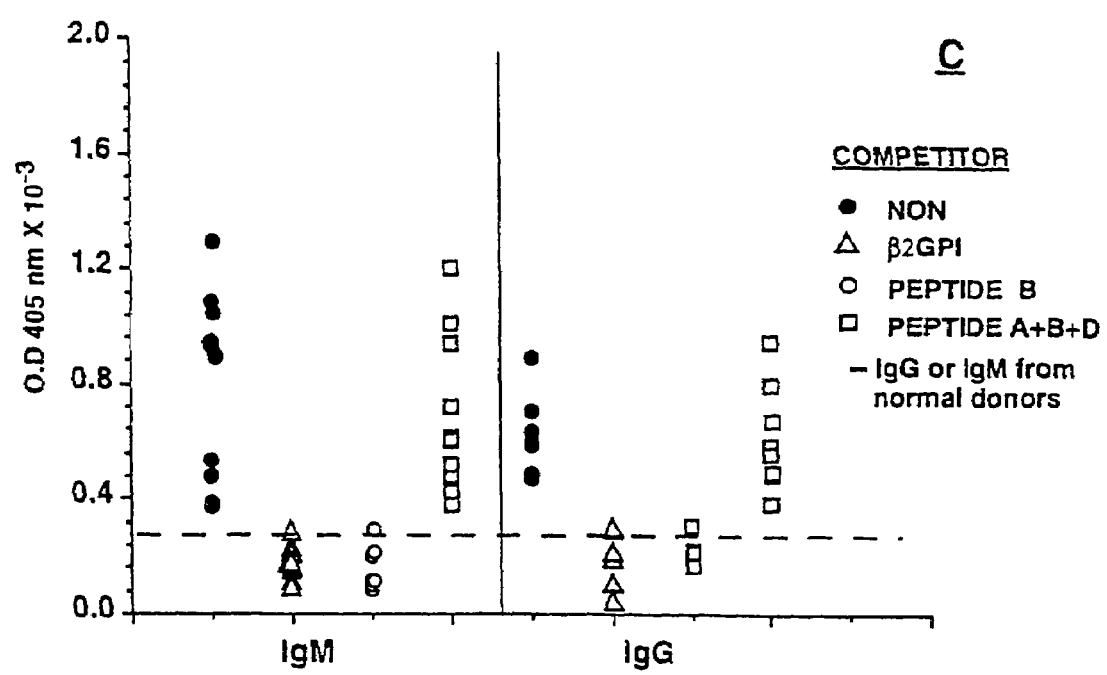

The specificity of the recognition of the studied anti-β2GPI epitopes A, B, C by anti-β2GPI Abs from APS patients was confirmed by competition assays in which specificity of binding of anti-β2GPI IgM and IgG from patients with APS to the inhibitory peptides was examined. The results are shown in FIGS. 6A–6C. Anti-β2GPI IgG and IgM affinity purified from APS patients (affinity purification of the antibodies was carried out by incubation of cardiolipin lyposomes with patients' sera overnight at 4° C. with rotation following sedimentation of the complexes (30000 rpm), elution of the bound Abs by KI 1M, extraction from the lyposomes by chloroform, and separation of the total anti-β2GPI IgM, IgG Abs into the different isotypes employing either anti-human-IgM-Sepharose or anti-human-IgG-Sepharose (Pharmacia)) were preincubated with β2GPI (triangles), specific peptide monomer (circles) or a cocktail of the other peptides as monomers (squares), and tested for their binding to the specific biotinylated peptide-coated ELISA plates. Anti-β2GPI IgM and IgG from APS patients recognized specifically ILA-1 corresponding peptide A, as shown in FIG. 6A, by competition with peptide A in comparison to peptide cocktail (B+C+D) as competitors (p<0.002). β2GPI elicits the anti-β2GPI IgM and IgG binding to peptide A, leading to the postulation that epitope A is exposed on the β2GPI molecule. On the other hand, anti-β2GPI IgM and IgG which were found to bind specifically peptide B (FIG. 6B), did not recognize the β2GPI molecule in fluid phase, since β2GPI could not abrogate the binding of anti-β2GPI to peptide B (p>0.5), pointing to the possibility that peptide B is a cryptic epitope of the β2GPI molecule. Peptide C, corresponding to H-3 anti-β2GPI mAb, was recognized specifically by anti-β2GPI IgM and IgG from APS patients (p<0.002). β2GPI molecule was able to reduce the anti-β2GPI binding to peptide C in fluid phase, pointing to the possibility that this epitope is exposed on the surface of the target molecule (FIG. 6C).

Example 8

The Effect of the Inhibitory Peptides A, B, C on anti-β2GPI Secretion by Hybridoma Cells Anti-β2GPI mAb secretion by human hybridoma cells named ILA-1, ILA-3, G-3 or human hybridoma secreting irrelevant immunoglobulin PE was studied by ELISA. The hybridoma cells were incubated in vitro with the peptides A, B, C or D as monomers, dimers or tetramers with St. The PE hybridoma cells were exposed to a cocktail of tetramer peptides St-tetraA+St-tetraB+St-tetraC+St-tetraD. The peptides were used at a concentration of 10 μM.

Figure 7:
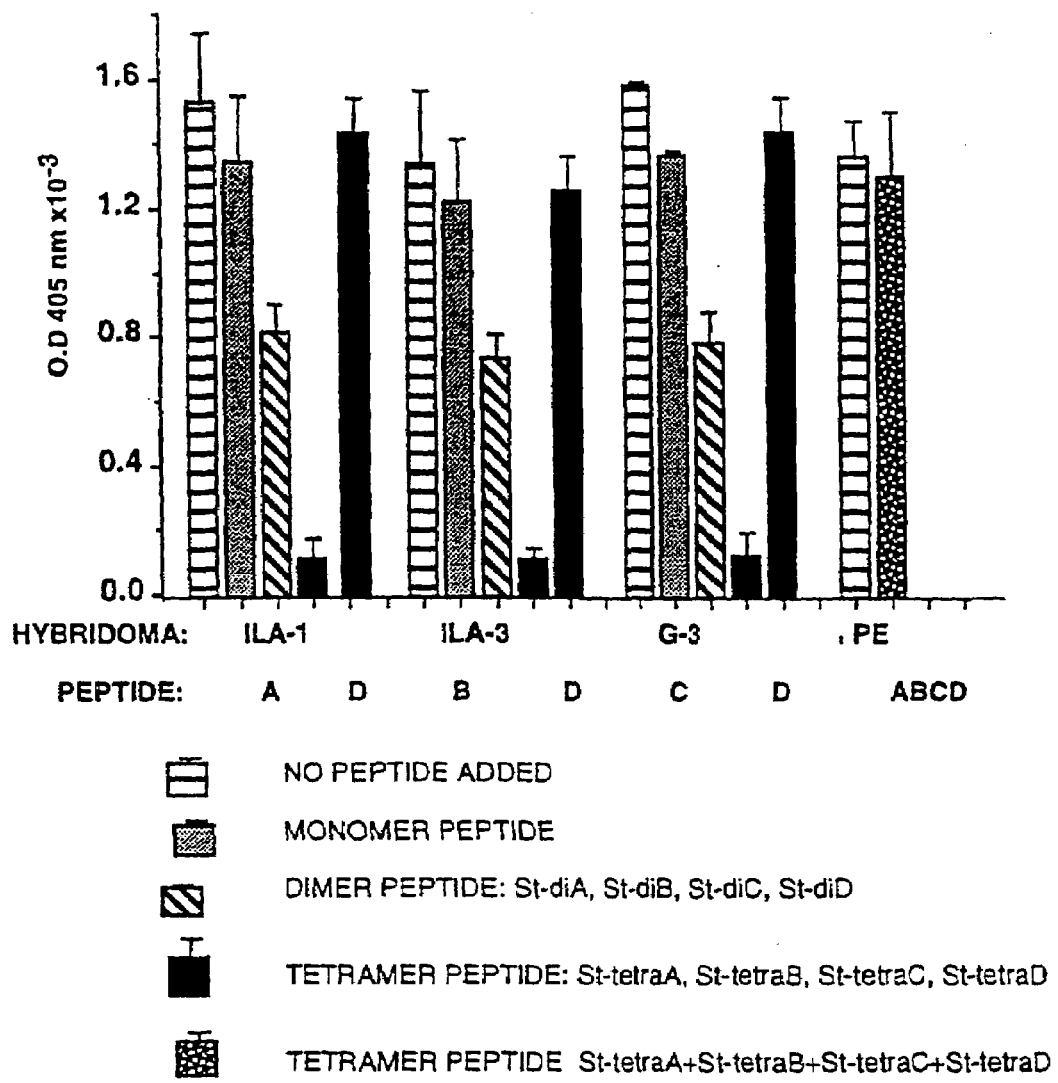
FIG. 7 is a bar graph showing prevention of secretion of anti-β2GPI ILA-1, ILA-3, G-3 mAbs by human hybridoma cells secreting them or an irrelevant immunoglobulin herein designated PE, upon exposure to the monomer peptides A, B, C, D, peptide dimers St-diA, St-diB, St-diC, St-diD, and peptide tetramers St-tetraA, St-tetraB, St-tetraC, St-tetraD. The PE hybridoma cells were exposed to a cocktail of tetramers St-tetraA+St-tetraB+St-tetraC. The peptides were used in concentration of 10 μM.

The results shown in FIG. 7 reveal that addition of St-tetraA to ILA-1 cells, St-tetraB to ILA-3 cells and St-tetraC to G-3 cells completely abrogated the antibody secretion (p<0.001), while irrelevant St-tetraD had no effect. Addition of a cocktail of the 4 tetramer peptides to irrelevant PE hybridoma cells had no effect on the Ab secretion. Administration of the specific dimer peptides A, B. C to the corresponding hybridoma cells abolished moderately, but significantly, the anti-β2GPI Ab secretion (p<0.03).

Example 9

Effect of the Inhibitory Peptides on Human anti-β2GPI Antibody Secretion

The effect of the inhibitory peptides A, B, C as tetravalent MAP with Lys on anti-β2GPI Abs secretion by PBL from APS patients was tested in vitro as described in Materials and Methods, section (1), with PBL derived from APS patient S, who was the source for the preparation of ILA-1 and ILA-3 mAbs, and from APS patient Y, whose anti-β2GPI Ab recognized peptide A. PBL from a human donor that does not produce anti-β2GPI Abs were used as control. The tetravalent peptides A, B, A+B, C, and D were used to test patient S, and A, B, and C to test patient Y. The results are shown in FIG. 8.

Figure 8:
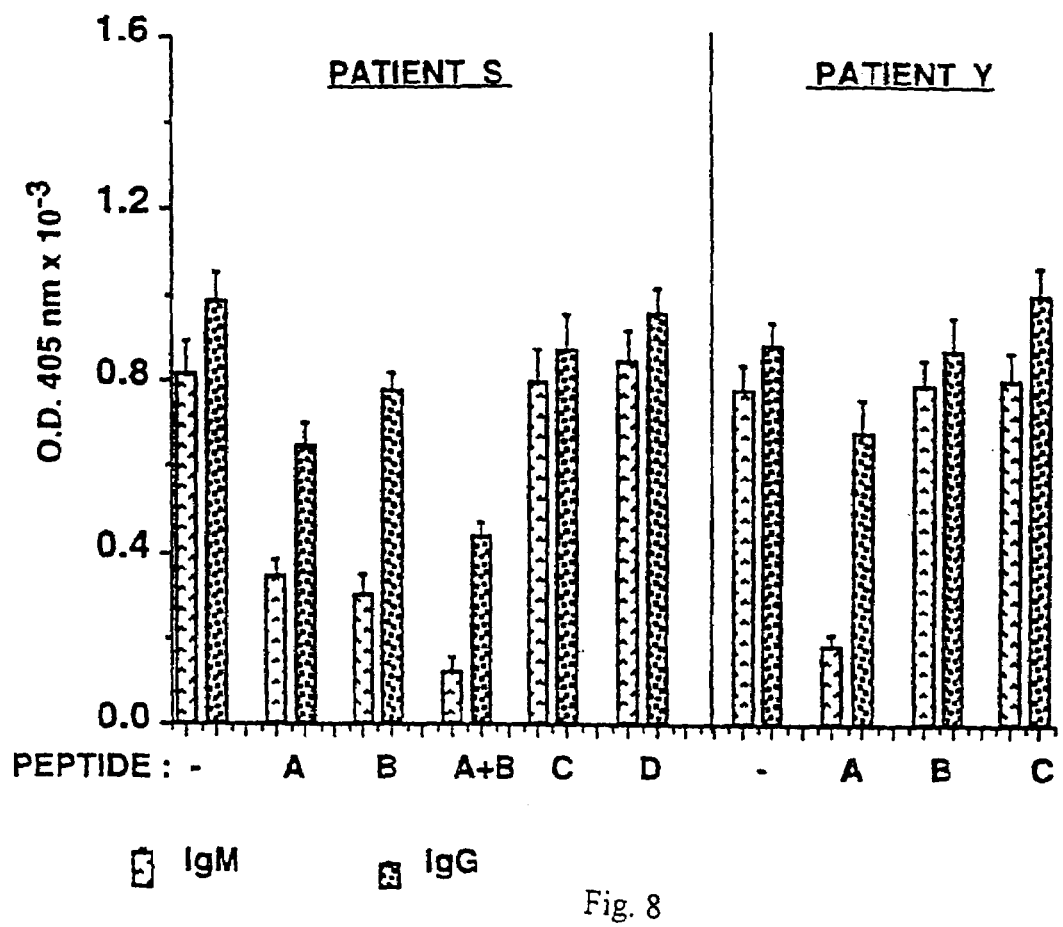
FIG. 8 is a bar graph showing anti-β2GPI antibody secretion by PBL from 2 human APS patients (designated S and Y) in vitro in the presence of the inhibitory tetravalent peptides A, B, C(S and Y), A+B (S) and control tetravalent peptide D (S). The peptides were used in concentration of 10 μM.

As shown in FIG. 8, the tetravalent peptides A and B inhibited specific anti-β2GPI Ab secretion by PBLs derived from patient S. IgM secretion was reduced to O.D 0.378±0.047, IgG secretion was reduced to O.D 0.625±0.037 in the presence of the tetravalent peptide A, in comparison to anti-β2GPI IgM and IgG secretion in the presence of the irrelevant tetravalent peptide D (O.D 0.827±0.063 and 0.934±0.083, p<0.001 and p<0.04, respectively). The tetravalent peptide A reduced the secretion of anti-β2GPI IgM (p<0.002) and of IgG (p<0.03) by PBL derived from APS patient S. The tetravalent peptide B inhibited significantly the anti-β2GPI IgM secretion (p<0.002) and IgG secretion (p<0.04) by PBL from APS patient S, but not by PBL originated from APS patient Y, p>0.5. The most pronounced inhibitory effect on anti-β2GPI IgM and IgG secretion was shown when a mixture of tetravalent peptides A+B was given to patient S (p<0.001 and p<0.002, respectively).

Example 10

Figure 9:
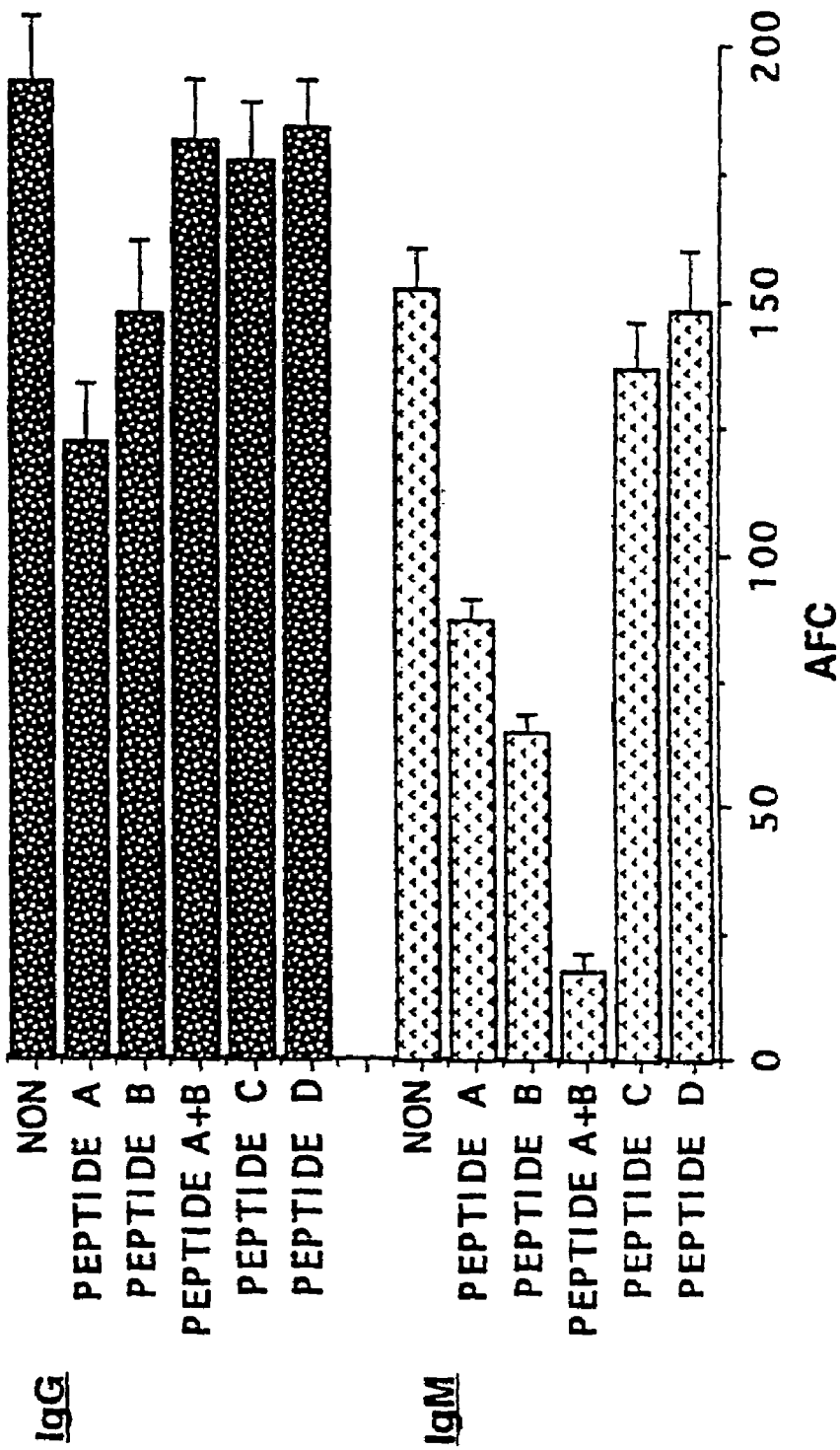
FIG. 9 is a bar graph showing the in vitro effect of the inhibitory tetravalent peptides A, B, C, A+B and control tetravalent peptide D on human anti-β2GPI antibody-forming cell (AFC) activity from an APS patient. Enriched B cell population from an APS patient, specific to β2GPI, were treated with the peptides at concentration of 10 μM for 8 h, washed and incubated overnight at 37° C. in an atmosphere of 7% $CO_2$. AFC activity was examined the day after, employing spot ELISA assay.

Effect of the Inhibitory Peptides as Monomers, Divalent and Tetravalent MAP on anti-β2GPI Antibody Forming Cell Activity Enriched population of anti-β2GPI B cells was studied for anti-β2GPI IgM and IgG AFC activity in the presence tetravalent inhibitory peptides A, B, A+B, and control D, by spot ELISA, as described in Materials and Methods, section (1). The results in FIG. 9 show significant abrogation in the number of IgM anti-β2GPI AFCs upon exposure to tetravalent peptide A, (37%), and inhibition of 40.5% of IgG anti-β2GPI AFCs (p<0.002). Exposure of the anti-β2GPI B cells to tetravalent peptide B resulted in significant reduction in the number of IgM anti-β2GPI AFCs by 59% (p<0.001) and 21.7% inhibition of anti-β2GPI IgG secretion (p<0.02) was observed. Synergistic effect was shown when the studied cells were treated with a mixture of tetravalent peptides A+B, that inhibited IgG anti-β2GPI AFCs by 47% and IgM by 82%, pointing to the possibility that there are additional epitope/s recognized by anti-β2GPI IgG. Tetravalent peptide C (anti-β2GPI corresponding epitope which is not recognized by the immunoglobulins from the studied patient S), and irrelevant tetravalent peptide D did not affect anti-β2GPI AFC activity (2–10%) p>0.5.

Figure 10A:
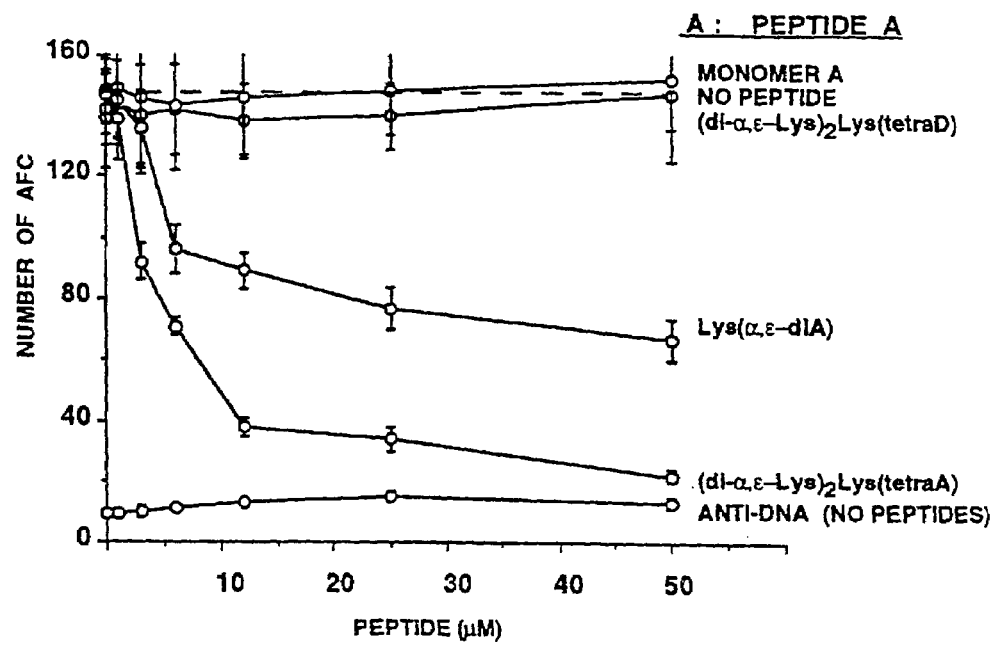
FIG. 10A: monomer A, divalent peptide A, and tetravalent peptides A, D.
Figure 10B:
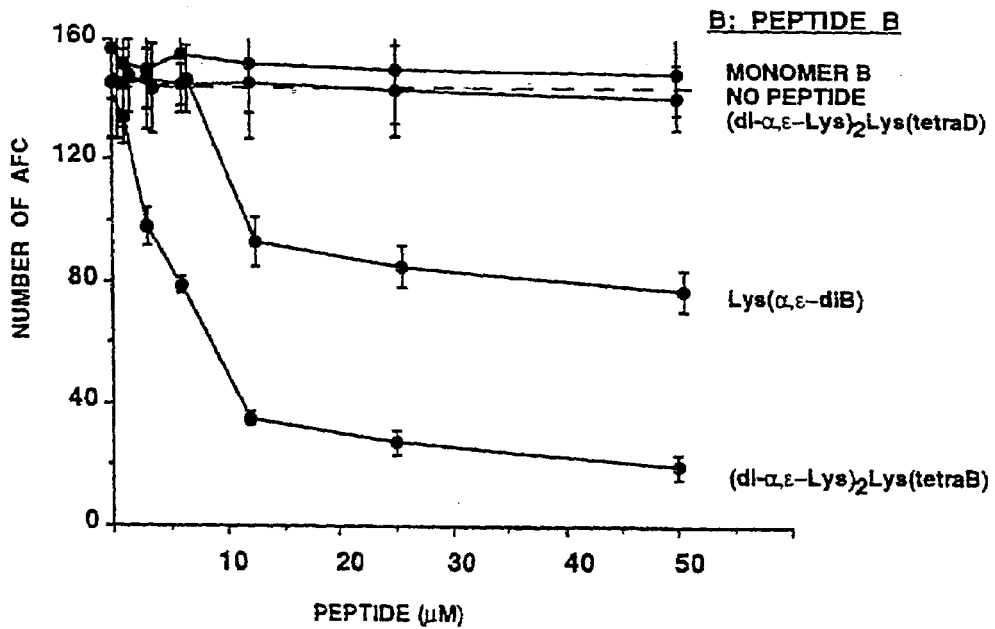
FIG. 10B: monomer B, divalent peptide B, and tetravalent peptides B, D.
Figure 10C:
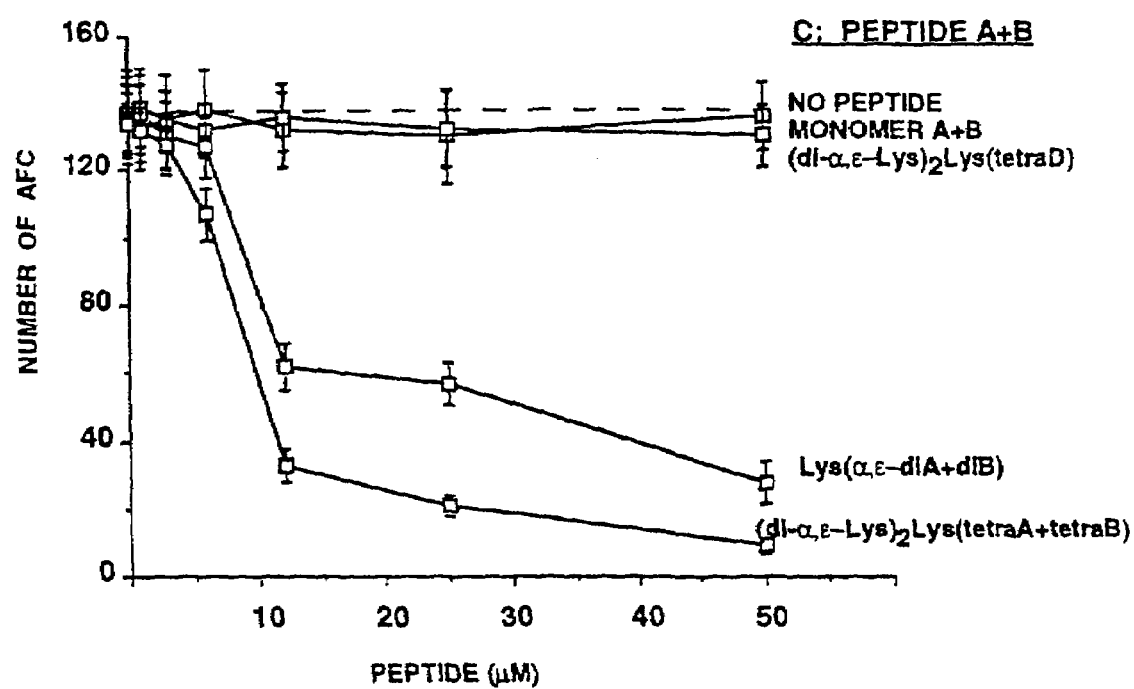
FIG. 10C: monomer A+B; divalent peptidea A+B, tetravalent peptides A+B, D.

Dose dependent studies on human anti-β2GPI AFC activity were carried out with enriched B cell population from an APS patient, specific to β2GPI, exposed to varying concentrations of the inhibitory peptides A, B, C as monomers, divalent and tetravalent peptides, and to irrelevant anti-DNA AFC as negative control. The results are shown in FIGS. 10A–C. FIG. 10A: monomer A, divalent peptide A, tetravalent peptide A and control peptide D. FIG. 10B: monomer B, divalent peptide B, tetravalent peptide B and control peptide D. FIG. 10C: FIG. 10C: monomer mixture A+B, divalent peptide mixture A+B, tetravalent peptide mixture A+B and control peptide D The results confirm the most significant inhibitory effect of the specific tetravalent peptide on antibody-forming cell activity (p<0.001 for all specific peptides and p>0.05 for irrelevant peptide).

Example 11

Detection of B Cell Epitopes in Mice

Figure 11:
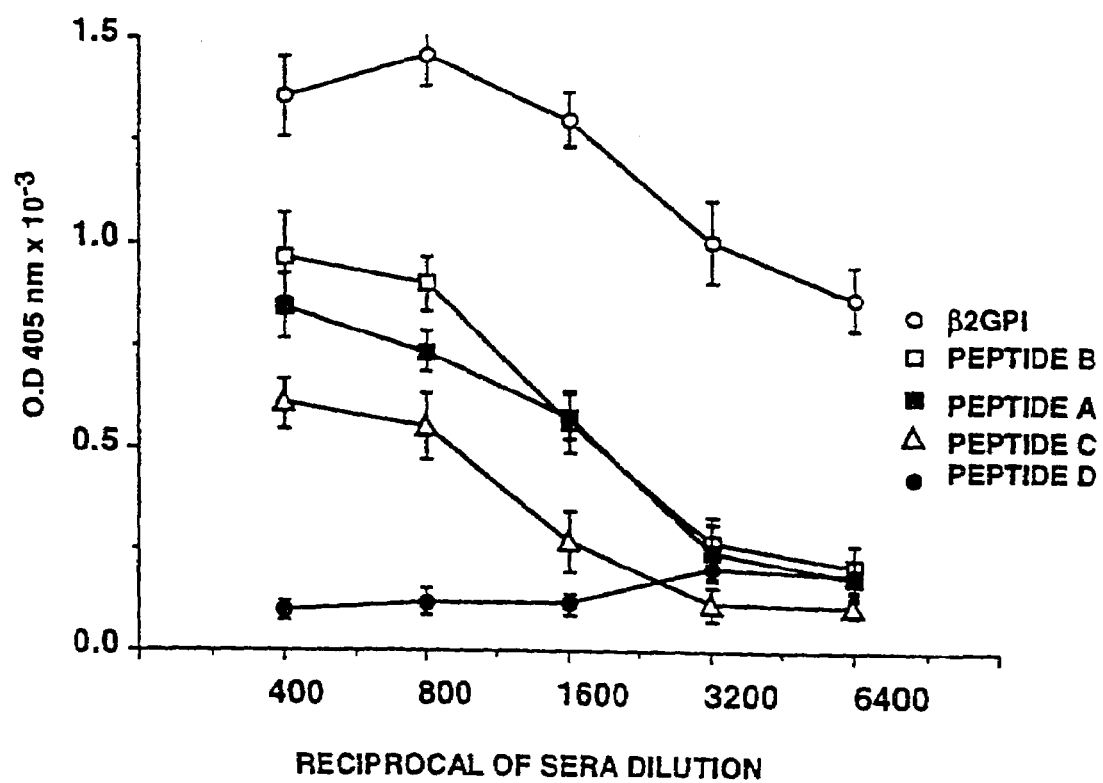
FIG. 11 shows the presence of B cell peptide epitopes in mice immunized with β2GPI. Sera of immunized mice were screened for the presence of mouse antibodies to peptide A, B and C, by ELISA, with streptavidin-coated plates followed by incubation with biotinylated peptide A, B, and C. Blocked plates (3% gelatin) were exposed to different dilutions of the sera. The binding was probed by anti-mouse IgG alkaline phosphatase.

BALB/c mice were immunized (day 0) in the hindfootpads with 10 μg β2GPI in Complete Freund's Adjuvant (CFA), Three weeks after, the mice received a booster injection of β2GPI in PBS. Sera of the mice (anti-β2GPI) were used to screen peptides for the presence of B cell epitopes, as follows: 96-well ELISA plates were coated with streptavidin overnight at 4° C., followed by incubation with biotinylated peptide monomers A, B, C, or D, β2GPI or BSA in PBS (100 μM) for 2 hours at room temperature. The ELISA plates were blocked with 3% gelatin, and the mouse sera were added thereto at different dilutions. Binding was probed with goat anti-mouse IgG alkaline phosphatase. The results depicted in FIG. 11 show that peptides A, B and C reacted specifically with antibodies from the immunized mice (p<0.001 for peptides A,B,C compared to peptide D), indicating the presence of B cell epitopes on the three peptides.

REFERENCES
1. Adamson P., Tighe M. and Pearson J D. (1996) *Cell Adhesion and Communication* 3:511.
2. Bakimer R., Guilburd B., Zurgil N. and Shoenfeld Y. (1993) *Clin. Immunol. Immunopathol* 69:97.
3. Blank M., Cohen J., Toder V. and Shoenfeld Y. (1991) *Proc. Natl. Acad. Sci.* (USA). 88:3069.
4. Carvalho D., Savage C O S., Black C M. and Pearson J. (1996) *J. Clin. Invest.* 97: 111.
5. DelPapa N., Guidali L., Sala A., Buccellati C., Khamashta M. A., Ichikawa K., Koike T., Balestrieri G., Tincani A., Hughes G. R. V. and Meroni P. L. (1997) *Arthritis. Rheum.* 40: 551–561
6. George J., Blank M., Levy Y., Grinbaum E., Cohen S., Damianovich M., Tincani A. and Shoenfeld Y. (1998) *Circulation.* 97:900
7. Green, N. M. (1965) *Biochem. J,* 4: 54
8. Hughes G. R. V., Harris E. N. and Gharavi A. E. (1986) *J. Rheumatol.* 13:486.
9. Hunt J. and Krilis S. A. (1994) *J. Immunol* 152:653.
10. Igarashi M., E. Matsuura, Y. Igarashi, H. Nagae, K. Ichikawa, D. A. Triplett and T. Koike (1996) *Blood* 87:3262.
11. Jaffe E A, Nachman RL, Becker CG, and Minick C R (1973) *J. Clin Invest* 52: 2745.
12. Kandiah D A and Krilis S A (1994) *Lupus* 3: 207.
13. McNeil H. P., C. N.Chesterman and S. A. Krilis (1991) *Adv. Immunol* 49:193.
14. McNeil H. P., R. J. Simpson, C.N.Chesterman and S. A. Krilis (1990) *Proc. Natl. Acad. Sci. USA* 87:4120.
15. Merrifield et al., (1997) *Methods Enzymol.* 289
16. Muller, G. M. et al. (1982) *Proc. Natl. Acad. Sci. USA* 79: 569.
17. Posnett D. N. et al., (1988) *J. Biol. Chem.* 263:1719.
18. Sahm et al., 1996, J. Pharm. Pharmacol. 48 (2): 197.
19. Schultze HE, Heide H and Haput H. (1961) *Naturwissenschften* 48: 719.
20. Scott J. K. and Smith G. P. (1990) *Science* 249:386.
21. Scott J K, Loganathan D, Easley RB, Gong X, and Goldstein, IJ (1992) *Proc. Natl. Acad. Sci. USA* 89: 5398.
22. Sheng Y., Sali A., Herbert H., Lahnstein J. and Krilis S. (1996) *J. Immunol* 157:3744.
23. Shi W., Chong B H., Chesterman C N. (1993) *Blood* 81: 1255.
24. Simantov R, LaSala JM, Lo SK, Gharavi AE, Sammaritano LR, Salmon J E and Silverstein RL. (1995) J Clin Invest 96: 2211.
25. Tam, J P. (1989) *Synthetic Peptides: Approaches to Biological Problems,* 3–8.
26. Tam, J P. (1988) *Proc. Natl. Acad. Sci. USA* 85: 5409..
27. Yayon, A, Aviezer D, Safran M, Gross JL, Cabilly S, Givol D and Katchalski-Katzir E (1993) *Proc. Natl. Acad. Sci. USA* 90: 10643.

The invention claimed is:

1. A synthetic peptide selected from the group consisting:
   (i) a peptide of SEQ ID NO:1 to SEQ ID NO: 7, of the sequences:
   Leu-Lys-Thr-Pro-Arg-Val (SEQ ID NO:1);
   Lys-Thr-Pro-Arg-Val-Thr (SEQ ID NO:2);
   Asn-Thr-Leu-Lys-Thr-Pro-Arg-Val-Gly-Gly (SEQ ID NO: 3);
   Lys-Asp-Lys-Ala-Thr-Phe-Gly-Thr-His-Asp-Gly (SEQ ID NO:4);
   Thr-Lys-Leu-Arg-Val-Tyr (SEQ ID NO:5);
   Thr-Leu-Leu-Arg-Val-Tyr (SEQ ID NO:6); and
   Cys-Ala-Thr-Leu-Arg-Val-Tyr-Lys-Gly-Gly (SEQ ID NO:7), and
   (ii) a peptide of (i) that is biotinylated.

2. The peptide according to claim 1 of SEQ ID NO:1.

3. The peptide according to claim 1 of SEQ ID NO:4.

4. The peptide according to claim 1 of SEQ ID NO:7.

5. The peptide according to claim 1 (ii) that is biotinylated.

6. The peptide according to claim 5, wherein the peptide is a peptide of SEQ ID NO:1 that is biotinylated.

7. The peptide according to claim 5, wherein the peptide is a peptide of SEQ ID NO:4 that is biotinylated.

8. The peptide according to claim 5, wherein the peptide is a peptide of SEQ ID NO:7 that is biotinylated.

* * * * *